(12) United States Patent
Lorton et al.

(10) Patent No.: US 7,462,618 B2
(45) Date of Patent: Dec. 9, 2008

(54) TREATMENT OF INFLAMMATORY AUTOIMMUNE DISEASES WITH ALPHA-ADRENERGIC ANTAGONISTS AND BETA-ADRENERGIC AGONISTS

(75) Inventors: Dianne Lorton, Avondale, AZ (US); Cheri Lubahn, Glendale, AZ (US)

(73) Assignee: Sun Health Research Institute, Sun City, AZ (US)

( * ) Notice: Subject to any disclaimer, the term of this patent is extended or adjusted under 35 U.S.C. 154(b) by 343 days.

(21) Appl. No.: 10/928,437

(22) Filed: Aug. 27, 2004

(65) Prior Publication Data

US 2005/0049256 A1 Mar. 3, 2005

Related U.S. Application Data

(60) Provisional application No. 60/498,367, filed on Aug. 27, 2003.

(51) Int. Cl.
*A61K 31/497* (2006.01)
*A61K 31/415* (2006.01)
*A61K 31/135* (2006.01)

(52) U.S. Cl. ............ 514/252.16; 514/400; 514/649

(58) Field of Classification Search ............ 514/252.16, 514/400, 649
See application file for complete search history.

(56) References Cited

U.S. PATENT DOCUMENTS 5,264,459 A * 11/1993 Chelmicka-Schorr et al. .... 514/646
5,513,661 A * 5/1996 Hubbard ..................... 128/898
6,610,905 B1 8/2003 Lira et al.
6,613,958 B1 9/2003 Neuhold et al.

FOREIGN PATENT DOCUMENTS

WO        WO 9221981        * 12/1992

OTHER PUBLICATIONS

Lubahn et al., "Chronic Treatment with Adrenergic Agents Attenuates the Inflammation and Bone Destruction associated with Adjuvant Arthritis (AA)", Society for Neuroscience Abstracts, (2001), (Biosis Abstract; 2001).*
Abrass, C., et al.: Characterization of the beta-adrenergic receptor of the rat peritoneal macrophage. *J Immunol* 135:1338-1341(1985).
Ackerman, N., et al.: Effects of naproxen on connective tissue changes in the adjuvant arthritic rat. *Arthritis Rheum* 22:1365-1374 (1979).
Aguilera, G., et al.: Differential regulation of hypothalamic pituitary corticotropin releasing hormone receptors during development of adjuvant-induced arthritis in the rat. *J Endocrinol* 153:185-91 (1997).
Albalas, J., et al.: Gi-mediated activation of the p21$^{ras}$-mitogen-activated protein kinase pathway by $\alpha_2$-adrenergic receptors expressed in fibroblasts. *J Biol Chem* 268:22235-22238 (1993).

Allen, J., et al.: Suppression of monocyte function and differential regulation of IL-1 and IL-1ra by IL-4 contribute to resolution of experimental arthritis. *J Immunol* 151 (1993) 4333-4351.
Arai, K., et al.: Cytokines: Coordinators of immune and inflammatory responses. *Ann Rev BioChem* 59:783-836 (1990).
Baerwald, C., et al.: Decreased density of beta-adrenergic receptors on peripheral blood mononuclear cells in patients with rheumatoid arthritis. *J Rheumatol* 19:204-210 (1992).
Baerwald, C., et al.: Impaired sympathetic influence on the immune response in patients with rheumatoid arthritis due to lymphocyte subset-specific modulation of beta 2-adrenergic receptors. *Br J Rheumatol* 36:1262-1269 (1997).
Baghai, M., et al.: Fatal sepsis in a patient with rheumatoid arthritis treated with etanercept. *Mayo Clin Proc* 76:573-575 (2001).
Bartik, M., et al.: Modulation of T cell proliferation by stimulation of the beta-adrenergic receptor: lack of correlation between inhibition of T cell proliferation and cAMP. *J Immunol* 154:408-21 (1993).
Bauman, G., et al.: Induction of cAMP-dependent protein kinase (PKA) activity in T cells after stimulation of the prostaglandin $E_2$ or the beta-adrenergic receptors: relationship between PKA activity and inhibition of anti-CD3 monoclonal antibody-induced T cell proliferation. *Cell Immunol* 158:182 (1994).
Bellinger, D., et al.: In R.Ader, D.L.Felten, and N.Cohen (eds.) *Psychoneuroimmunology. III*, Academic Press, San Diego, pp. 55-111 (2000).
Bellinger, D., et al.: Noradrenergic sympathetic innervation of thymus, spleen, and lymph nodes: Aspects of development, aging and plasticity in neural immune interaction. In JW. Hadden, K. Masek and G. Nistico (Eds.) *Interactions Among Central Nervous System, Neuroendocrine and Immune Systems*, Pythagora Press, Roma, Milano, pp. 35-66 (1989).
Besedovsky, J, et al.: Immunoregulation mediated by the sympathetic nervous system *Cell Immunol* 48:346-355 (1979).
Betz, M. et al.: Prostaglandin $E_2$ inhibits production of Th1 lymphokines but not of Th2 lymphokines. *J Immunol* 146:108-13 (1991).
Binderup, L., et al.: Splenic suppressor cells in adjuvant arthritic rats: effect of D-penicillamine. *Agents and Actions* 7 Suppl. 199-203 (1980).
Brown, S., et al.: Tumor necrosis factor antagonist therapy and lymphoma development: twenty-six cases reported to the Food and Drug Administration. *Arthritis Rheum* 46:3151-3158 (2002).
Burchiel, S., et al.: Augmentation of the in vitro humoral immune response by pharmacologic agents. II: The comparison of the effects of antiproliferative agents with dibutyryl cAMP. *Immunopharmacol* 1:151-163 (1979b).

(Continued)

*Primary Examiner*—Raymond J Henley, III
(74) *Attorney, Agent, or Firm*—Jennings Strouss & Salmon; Joseph W. Mott

(57) ABSTRACT

The present invention discloses a novel compound and method for the treatment of inflammatory autoimmune diseases, for example, rheumatoid arthritis, using α-adrenergic antagonists and β-adrenergic agonists in combination. Treatment of animals, namely humans, with an α-adrenergic antagonist, preferably, phentolamine, and a β-adrenergic agonist, preferably terbutaline, in combination can significantly suppress the joint destruction and inflammation due to disease in these animals.

31 Claims, 5 Drawing Sheets

OTHER PUBLICATIONS

Burchiel, S., et al.: Augmentation of the in vitro humoral immune response by pharmacologic agents I: An explanation of the differential enhancement of humoral immunity via agents that elevate cAMP. *Immunopharmacol* 1:137-150 (1979a).

Burmester, G., et al.: Differential expression of Ia antigen by rheumatoid synovial lining cells. *J Clin Invest* 80:595-604 (1987).

Burmester, G., et al.: Mononuclear phagocytes and rheumatoid synovitis: mastermind or workhorse in arthritis? *Arthritis Rheum* 40:5-18 (1997).

Camilleri, J., et al.: The effect of free and liposome-encapsulated clodronate on the hepatic mononuclear phagocyte system in the rat. *Clin Exp Immunol* 99:269-275 (1995).

Charles, P., et al.: Regulation of cytokines, cytokine inhibitors, and acute-phase proteins following anti-TNF-alpha therapy in rheumatoid arthritis. *J Immunol* 163:1521-1528 (1999).

Chelmicka-Schorr, E., et al.: The beta 2-adrenergic agonist terbutaline suppresses acute passive transfer experimental autoimmune myasthenia gravis (EAMG), *Int J Immunopharmacol* 15:19-24 (1993).

Chelmicka-Schorr, E., et al.: The beta-adrenergic agonist isoproterenol suppresses experimental allergic encephalomyelitis in Lewis rats. *J NeuroImmuno* 25:203-207 (1989).

Chen, D., et al.: Interleukin 2 transcription factors as molecular targets of cAMP inhibition: delayed inhibition kinetics and combinatorial transcription roles. *J Exp Med* 179:931-42 (1994).

Cook, S., et al.: Inhibition by cAMP of Ras-dependent activation of Raf. *Science* 262:1069-1072 (1993).

Damoiseaux, J., et al.: Expression of the ED3 antigen on rat macrophages in relation to experimental autoimmune diseases. *Immunobiology* 84:311-320 (1992).

Dijkstra, C., et al.: Macrophages and dendritic cells in antigen-induced arthritis: an immunohistochemical study using cryostat sections of the whole knee joint of rat. *Scand J Immunol* 26:513-523 (1987).

Edmonds, J., et al.: Anti-rheumatic drugs: a proposed new classification. *Arthritis Rheum* 36:336-306 (1993).

Elenkov, I., et al.: Modulatory effects of glucocoricoids and catecholamines on human interleukin-12 and interleukin-10 production: clinical implications. *Proc Assoc Amer Physic* 108:374-381 (1996).

Elliott, M., et al.: Randomised double-blind comparison of chimeric monoclonal antibody to tumour necrosis factor α (cA2) versus placebo in rheumatoid arthritis. *Lancet* 344:1105-1110 (1994).

Feige, U., et al.: Anti-interleukin-1 and anti-tumor necrosis factor-alpha synergistically inhibit adjuvant arthritis in Lewis rats. *Cell Mol Life Sci* 57:1457-1470 (2000).

Feige, U., et al.: Combining anti-IL-1 and anti-TNF treatments provides better efficacy in rat adjuvant arthritis than does either agent alone. *Arthritis Rheum* 452:S383 (1999).

Feldmann, M., et al.: Anti-TNF-alpha therapy of rheumatoid arthritis: What have we learned? *Annu Rev Immunol* 19:163-196 (2001).

Felten, D., et al.: Noradrenergic sympathetic neural interactions with the immune system: structure and function. *Immunol Rev* 100:225-260 (1987).

Fox, D.: The role of T cells in the immunopathogenesis of rheumatoid arthritis. *Arthritis Rheum* 40:598-609 (1997).

Fries, J., et al.: Measurement of patient outcome in arthritis. *Arthritis Rheum* 23:137-145 (1980).

Hart, P., et al.: Regulatory effects of IL-13 on synovial fluid macrophages and blood monocytes from patients with inflammatory arthritis. *Clin Exp Immuno* 99:331-337 (1995).

Hasku, G., et al.: Regulation of cytokine and chemokine production by transmitters and co-transmitters of the autonomic nervous system. *Biochem Pharmacol* 56:1079-1087 (1998).

Hawes, B., et al.: Distinct pathways of Gi- and Gq-mediated mitogen-activated protein kinase activation. *J Biol Chem* 270:17148-17153 (1995).

Heijnen, C., et al.: Functional alpha 1-adrenergic receptors on leukocytes of patients with polyarticular juvenile rheumatoid arthritis. *J NeuroImmunol* 71: 223-226 (1996).

Hemler, M., et al.: Antigenic stimulation regulates the level of expression of interleukin 2 receptor on human T cells. *Proc Nat Acad Sci USA*, 81:2171-5 (1984).

Henderson, B., et al.: Production of interleukin 1 in the joint during the development of antigen-induced arthritis in the rabbit. *Clin Exp Immunol* 74:371-376 (1988).

Hendricks, P., et al.: Beta-agonists can depress oxidative metabolism of alveolar macrophages. *Agents and Actions* 19:353-354 (1986).

Hom, T., et al.: In vivo administration with IL-1 accelerates the development of collagen-induced arthritis in mice. *J Immunol* 141:834-841 (1988).

Ignatowski, T., et al.: Regulation of macrophage-derived tumor necrosis factor production by modification of adrenergic receptor sensitivity. *J Neuroimmunol* 61:61-70 (1995).

Iguchi, T., et al.: Electron microscopic study of rheumatoid synovial vasculature. Intimate relationship between tall endothelium and lymphoid aggregation. *J Clin Invest* 77:355-361 (1986).

Iguchi, T., et al.: Electron microscopic study of HLA-DR monocyte/macrophage staining cells in the rheumatoid synovial membrane. *Arthritis Rheum* 29:600-613 (1986).

Issekutz, A., et al.: The role of tumour necrosis factor-alpha and IL-1 in polymorphonuclear leucocyte and T-lymphocyte recruitment to joint inflammation in adjuvant arthritis. *Clin Exp Immunol* 97:26-32 (1994).

Johnson, W., et al.: Macrophage activation in rat models of inflammation and arthritis. Systemic activation precedes arthritis induction and progression. *Arthritis Rheum* 29:1122-1130 (1986).

Joosten, L., et al.: Role of interleukin-4 and interleukin-10 in murine collagen-induced arthritis; protective effect of interleukin-4 and interleukin-10 treatment on cartilage destruction. *Arth Rheum* 40:249-260 (1997).

Kalliomaki, J., et al.: Axon reflex sweating in rheumatoid arthritis. *Ann Rheum Dis* 22:46-49 (1963).

Karsh, J, et al.: Lymphocyte depletion by continuous flow cell centrifugation in rheumatoid arthritis: clinical effects. *Arthritis Rheum*, 22:1055-1059 (1979).

Kasama, T., et al.: Interleukin-10 expression and chemokine regulation during the evolution of murine type II collagen-induced arthritis. *J Clin Invest* 95:2868-2876 (1995).

Katsikis, P., et al.: Immunoregulatory role of interleukin 10 in rheumatoid arthritis. *J Exp Med* 179:1517-1527 (1994).

Keffer, J., et al.: Transgenic mice expressing human tumour necrosis factor: a predictive genetic model of arthritis. *EMBO J* 10:4025-4031 (1991).

Khansari, D., et al.: Effects of stress on the immune system. *Immunol Today* 11:170-175 (1990).

Kim, D., et al. The beta 2-adrenergic agonist terbutaline suppresses experimental allergic neuritis in Lewis rats. *J NeuroImmunol* 51:177-183 (1994).

Kinne, R., et al.: Macrophages in rheumatoid arthritis. *Arth Res* 2:189-202 (2000).

Kinne, R., et al.: Long-term amelioration of rat adjuvant arthritis following systemic elimination of macrophages by clodronate-containing liposomes. *Arthritis Rheum* 38:1777-1790 (1995).

Kinne, R., et al.: Treatment of rat arthritides with clodronate-containing liposomes. *Scand J Rheumatol* 23:83-89 (1995).

Klareskog, L., et al.: Immune functions of human synovial cells: phenotypic and T cell regulatory properties of macrophages-like cells that express HLA-DR. *Arthritis Rheum*, 25:488-501 (1982).

Kroemer, G., et al.: Immunoregulation by cytokines. *Crit Rev Immunol* 13:163-191 (1993).

Kruszewska, B., et al.: Alterations in cytokine and antibody production following chemical sympathectomy in two strains of mice. *J Immunol* 155 (1995) 4613-20.

Kuis, W., et al.: The autonomic nervous system and the immune system in juvenile rheumatoid arthritis. *Brain Behav Immun* 10:387-98 (1996).

Kupfer, A., et al.: Cell biology of cytotoxic and helper T-cell functions. *Annu Rev Immunol* 7:309-337 (1989).

Leden, I., et al.: Autonomic nerve function in rheumatoid arthritis of varying severity. *Scand J Rhematol* 12:166-70 (1983).

Lee, J., et al.: Life-threatening histoplasmosis complicating immunotherapy with tumor necrosis factor alpha antagonist infliximab and itanercept. *Arthritis Rheum* 46:2565-2570 (2002).

Lee, J., et al.: Suppressed IL-2 production and response in AA rats: role of suppressor cells and the effect of auranofin treatment. *J Rheumatol* 12:885-891 (1985).

Leeb, B., et al.: Anti-TNF-alpha therapy as a new option in treatment of rheumatoid arthritis? *Wien Med Wochenschr* 149:554-557 (1999).

Llorente, L., et al.: In vivo production of interleukin-10 by non-T cells in rheumatoid arthritis, Sorgren's syndrome, and systemic lupus erythematosius: a potential mechanism of B lymphocyte hyperactivity and autoimmunity. *Arthritis Rheum* 17:1647-1655 (1994).

Lorton, D., et al.: Potential use of drugs that target neural-immune pathways in the treatment of rheumatoid arthritis and other autoimmune diseases. *Curr Drug Targets Inflammation & Allergy* 2:1-30 (2003).

Lorton, D., et al.: Local application of capsaicin into the draining lymph node attenuates expression of adjuvant-induced arthritis. *Neuroimmunomodulation* 7:115-125 (2000).

Lorton, D., et al.: Changes in the density and distribution of sympathetic nerves in spleens from Lewis rats with adjuvant-induced arthritis suggests an injury and sprouting response occurs. *J Comp Neurol* (accepted) (2004).

Lorton, D., et al.: Norepinephrine content in primary and secondary lymphoid organs is altered in rats with adjuvant-induced arthritis. *Mech Aging Dev* 94:145-163 (1997).

Lorton, D., et al.: Loss of noradrenergic nerves in secondary lymphoid tissue from rats with adjuvant arthritis parallels loss of nerve growth factor containing target lymphoid cells. *Brain Behav Immun* 14:112 (2000).

Lorton, D., et al.: Introduction to biological signaling in Psychoneuroimmunology. In R.Ader, D.L.Felten, and N.Cohen (eds.), *Psychoneuroimmunology III*, Academic Press, San Diego, pp. 113-160 (2000).

Lorton, D., et al.: Dual role for noradrenergic innervation of lymphoid tissue and arthritic joints in adjuvant-induced arthritis. *Brain Behav Immun* 13:315-334 (1999).

Lorton, D.: Advancements toward treatment of rheumatic disease in the 1990s. *Arizona Geriatrics Society* 4:10-11 (1999).

Lubahn, C. et al.: The importance of timing of adrenergic drug delivery in relation to the induction and onset of adjuvant-induced arthritis. *Brain Behav Immun* (accepted) 2004.

Lubberts, D., et al.: Regulatory role of interleukin 10 in joint inflammation and cartilage destruction in murine streptococcal cell wall (SCW) arthritis. More therapeutic benefit with Il-4/Il-10 combination therapy than with IL-10 alone. *Cytokine* 10: 361-369 (1998).

Malfait, A., et al.: The $beta_2$-adrenergic agonist salbutamol is a potent suppressor of established collagen-induced arthritis: mechanisms of action. *J Immunol* 162:6278-6283 (1999).

Mayordomo, L., et al.: Pulmonary military tuberculosis in a patient with anti-TNF-alpha treatment. *Scand J Rheumatol* 31:44-45 (2002).

McInnis, I., et al. The role of interleukin-15 in T cell migration and activation in rheumatoid arthritis. *Nature Med* 2:175-182 (1996).

Meenan, R., et al.: Measuring health status in arthritis: The Arthritis Impact Measurement Scales. *Arthritis Rheum* 23:146-152 (1980).

Miller, L..., et al.: The loss of sympathetic nerve fibers in the synovial tissue of patients with rheumatoid arthritis is accompanied by increased norepinephrine release from synovial macrophages. *FASEB J* 14:2097-2107 (2000).

Miltenburg, A., et al.: T cells cloned from human rheumatoid synovial membrane functionally represent the Th1 subset. *Scand J Immunol* 35:603-610 (1992).

Mohan, N., et al.: Demyelination occurring during anti-tumor necrosis factor alpha therapy for inflammatory arthritides. *Arthritis Rheum* 44:2862-2869 (2001).

Monastra, G. et al.: •-adrenergic receptors mediate in vivo the adrenaline inhibition of lipopolysacchride-induced tumor necrosis factor release. *Immunol Lett* 38:127-130 (1993).

Mosmann, T., et al.: Two types of mouse helper T cell clone: implications for immune regulation. *Immunol Today* 8:233-40 (1987).

Mosmann, T., et al.: Diversity of cytokine synthesis and function of mouse CD4+ T cells. *Immunol Rev* 123:209-229 (1991).

Mussener, A., et al.: TNF-alpha dominates cytokine mRNA expression in lymphoid tissues of rats developing collagen- and oil-induced arthritis. *Scand J Immunol* 42:128-34 (1995).

Panina-Bordignon, P., et al.: Beta2-agonists prevent Th1 development by selective inhibition of interleukin 12. *J Clin Invest* 100: 1513-1519 (1997).

Paul, W., et al.: Lymphocyte responses and cytokines. *Cell* 76:241-251 (1994).

Perry, F., et al.: Altered autonomic function in patients with arthritis or with chronic myofascial pain. *Pain* 39:77-84 (1989).

Piatier-Tonneau, D., et al.: T-suppressor lymphocytes regulation of adjuvant arthritis in two inbred stains of rats. *Clin Rheumatol 1*:Eular Workshop, 645-51 (1982).

Piguet, P., et al.: Evolution of collagen arthritis is arrested by treatment with anti-tumor necrosis factor (TNF) antibody or recombinant soluble TNF receptor. *Immunol* 77:510-514 (1992).

Probert, L., et al.: Type I interleukin-1 receptor acts in series with tumour necrosis factor (TNF) to induce arthritis in TNF-transgenic mice. *Eur J Immunol* 24:1794-1797 (1995).

Quayle, A., et al.: Rheumatoid inflammatory T-cell clones express mostly Th1 but also Th2 and mixed (Th0-like) cytokine patterns. *Scand J Immunol* 38:75-82 (1993).

Ramer-Quinn, D., et al.: Activated T helper 1 and T helper 2 cells differentially express the β-2-adrenergic receptor. *J Immunol*, 159:4857-4867 (1997).

Roth, S., et al.: Anti-TNF-alpha monoclonal antibodies (infliximab) and tuberculosis: apropos of 3 cases. *Rev Med Intern* 23:312-316 (2002).

Rouppe van der Voort, C., et al.: Neuroendocrine mediators up-regulate alpha1b- and alpha1d-adrenergic receptor subtypes in human monocytes. *J NeuroImmunol* 1:165-73 (1999).

Sanders, V. et al.: Role of alpha-adrenoceptor activation in modulating the murine primary antibody response in vitro. *J Pharmacol Exp Ther* 232:395-400 (1985).

Sanders, V., et al.: Differential expression of the $β_2$-adrenergic receptor by Th1 and Th2 clones: implications for cytokine production and B cell help. *J Immunol* 158:4200-10 (1997).

Saxne, T., et al.: Detection of tumor necrosis factor α but not tumor necrosis factor β in rheumatoid arthritis synovial fluid and serum. *Arthritis Rheum* 31:1041-1045 (1988).

Scott, P.: IFN-γ modulates the early development of Th1 and Th2 responses in a murine model of *Cutaneous leishmaniasis*. *J Immunol* 147:3149-3155 (1991).

Scott, P.: Selective differentiation of CD4+ T helper cell subsets. *Curr Opin Immunol* 5:391-397 (1993).

Seitz, M., et al.: Characterization of blood mononuclear cells of rheumatoid arthritis patients. I. Depressed lymphocyte proliferation and enhanced prostanoid release from monocytes. *Clin Immunol Immunopathol* 25:405-416 (1982).

Severn, A., et al.: Regulation of tumor necrosis factor production by adrenaline and •-adrenergic agonists. *J Immunol* 148:3441-3445 (1992).

Sher, A., et al.: Role of T-cell derived cytokines in the down regulation of immune responses in parasitic and retroviral infection. *Immunol Rev* 127:183-204 (1992).

Snapper, C., et al.: Interferon-γ and B cell stimulatory factor-1 reciprocally regulate Ig isotype production. *Science* 944-7 (1987).

Spengler, R., et al.: Stimulation of alpha-adrenergic receptor augments the production of macrophage-derived tumor necrosis factor. *J Immunol* 145:1430:1434 (1990).

Spengler, R., et al.: Endogenous norepinephrine regulates tumor necrosis factor-alpha production from macrophages in vitro. *J Immunol* 152:3024-3031 (1994).

St. Clair, E.: Infliximab treatment for rheumatic disease: clinical radiological efficacy. *Ann Rheum Dis* 61:67-69 (2002).

Stevens, T., et al.: Regulation of antibody isotype secretion by subsets of antigen-specific helper T cells. *Nature* 334:255-8 (1988).

Suberville, S., et al.: Regulation of interleukin-10 production by_-adrenergic agonists. *Eur J Immunol* 26:2601-2605 (1996).

Swanson, M., et al.: IFN-gamma production by Th1 cells generated from naïve CD4+ T-cells exposed to norepinephrine. *J Immunol* 166:232-240 (2001).

Szelenyi, J., et al.: Contribution of differently localized alpha 2- and beta-adrenoceptors in the modulation of TNF-alpha and IL-10 production in endotoxemic mice. *Ann NY Acad Sci* 917:145-153 (2000).

Tagaya, Y., et al.: IL-15: a pleiotropic cytokine with diverse receptor/signaling pathways whose expression is controlled at multiple levels. *Immunity* 4:329-336 (1996).

Taylor, P.: Anti-TNF alpha therapy for rheumatoid arthritis: an update. *Intern Med* 42:15-20 (2003).

Tenenbaum, J, et al.: Leukapheresis in severe rheumatoid arthritis. *Ann Rheum Dis* 3:40-44 (1979).

Tetta, C., et al.: Tumour necrosis factor in serum and synovial fluid of patients with active and severe rheumatoid arthritis. *Ann Rheum Dis* 49:665-667 (1990).

Thorbecke, G., et al.: Involvement of endogenous tumour necrosis factor $\alpha$ and transforming growth factor $\beta$ during induction of collagen type II arthritis in mice. *Proc Natl Acad Sci USA* 89:7375-7379 (1992).

Trinchieri, G.: The role of interleukin-12 in the immune response, disease and therapy. *Immunol Today* 15:460-463 (1994).

Trinchieri, G.: Interleukin-12 and its role in the generation of $T_H1$ cells. *Immunol Today*, 14:335-8 (1993).

Tsuruta, L.., et al.: Cyclic AMP inhibits expression of the IL-2 gene through the nuclear factor of activated T cells (NF-AT) site, and transfection of NF-AT cDNAs abrogates the sensitivity of EL-4 cells to cyclic AMP. *J Immunol* 15:45255-64 (1995).

Unanue, E., et al.: The basis for the immunoregulatory role of macrophages and other accessory cells. *Science* 237:551-557 (1987).

Van den Berg, T., et al.: Sialoadhesin on macrophages: its identification as a lymphocyte adhesion molecule. *J Exp Med* 176:647-655 (1992).

Van der Poll, T., et al.: Epinephrine inhibits tumor necrosis factor-alpha and potentiates interleukin 10 production during human endotoxemia. *J Clin Invest* 97:713-719 (1996).

Van Lent, P., et al.: Phagocytic synovial lining cells in chronic experimental arthritis: downregulation of synovitis by C12MDP-liposomes. *Rheumatol Int* 13:221-228 (1994).

Van Lent, P., et al.: In vivo role of phagocytic synovial lining cells in onset of experimental arthritis. *Am J Pathol* 143:1226-1237 (1993).

Verschure, P., et al.: Macrophages and dendritic cells during the early stages of antigen-induced arthritis in rats: immunohistochemical analysis of cryostat sections of the whole knee joint. *Scand J Immunol* 29:371-381 (1989).

Wacholtz, M., et al.: Characterization of the 3',5'-cyclic adenosine monophosphate-mediated regulation of IL2 production by T cells and Jurkat cells. *Cell. Immunol* 135:285-98 (1991).

Walmsley, M., et al.: Interleukin-10 inhibition of the progression of established collagen-induced arthritis. *Arthritis Rheum* 39:495-503 (1996).

Weinblatt, M., et al.: A trial of etanercept, a recombinant tumor necrosis factor receptor Fc Fusion protein, in patients with rheumatoid arthritis receiving methotrexate. *N Engl J Med* 340:253-259 (1999).

Wiegmann, K. et al.: Beta-adrenergic agonists suppress chronic/relapsing experimental allergic encephalomyelitis (CREAE) in Lewis rats. *J NeuroImmunol* 56:201-206 (1995).

Williams, R., et al.: Anti-tumor necrosis factor ameliorates joint disease in murine collagen-induced arthritis. *Proc Natl Acad Sci USA* 89:9784-9788 (1992).

Winitz, S., et al.: Involvement of Ras and Raf in the Gi-coupled acetycholine muscarinic M2 receptor activation of mitogen-activated protein (MAP) kinase and MAP kinase. *J Biol Chem* 269:19191-19199 (1993).

Yeaden, C., et al.: Lymphapheresis in rheumatoid arthritis. The clinical and laboratory effects of a limited course of cell depletion. *Clin Exp Rheumatol* 1:119-24 (1983).

Yssel, H., et al.: Borrelia burgdorferi activates a T helper type 1-like T cell subset in Lyme arthritis. *J Exp Med* 174:593-601 (1991).

Zinyama, R., et al.: Adrenaline suppression of the macrophage nitric oxide response to lipopolysaccharide is associated with differential regulation of tumor necrosis factor-alpha and interleukin-10. *Immunol* 103: 439-446 (2001).

Robinson, W., et al.: Demyelinating and neurologic events reported in association with tumor necrosis factor alpha antagonists, Arthritis Rheum 44:1977-83, (Sep. 2001).

\* cited by examiner

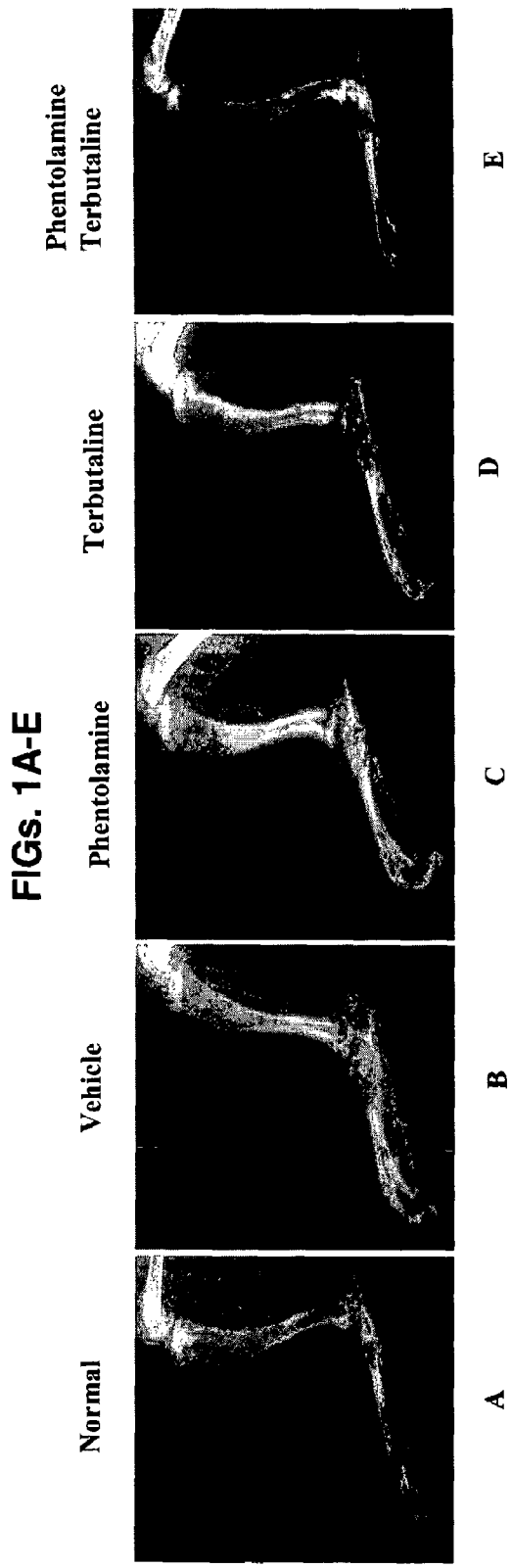
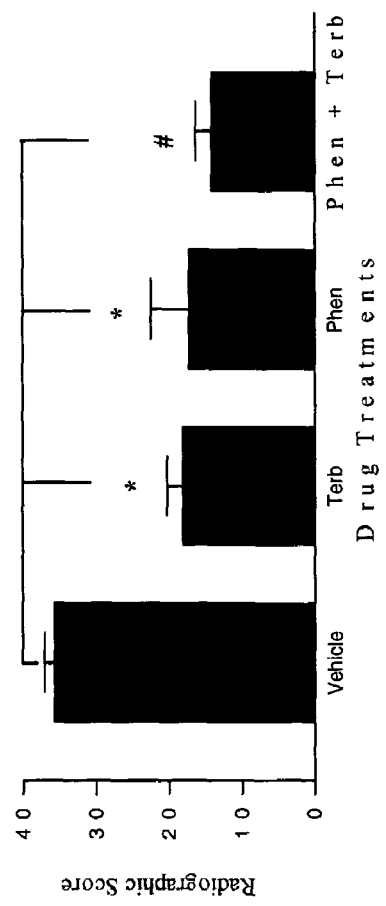
FIGs. 1A-E
FIG. 1F

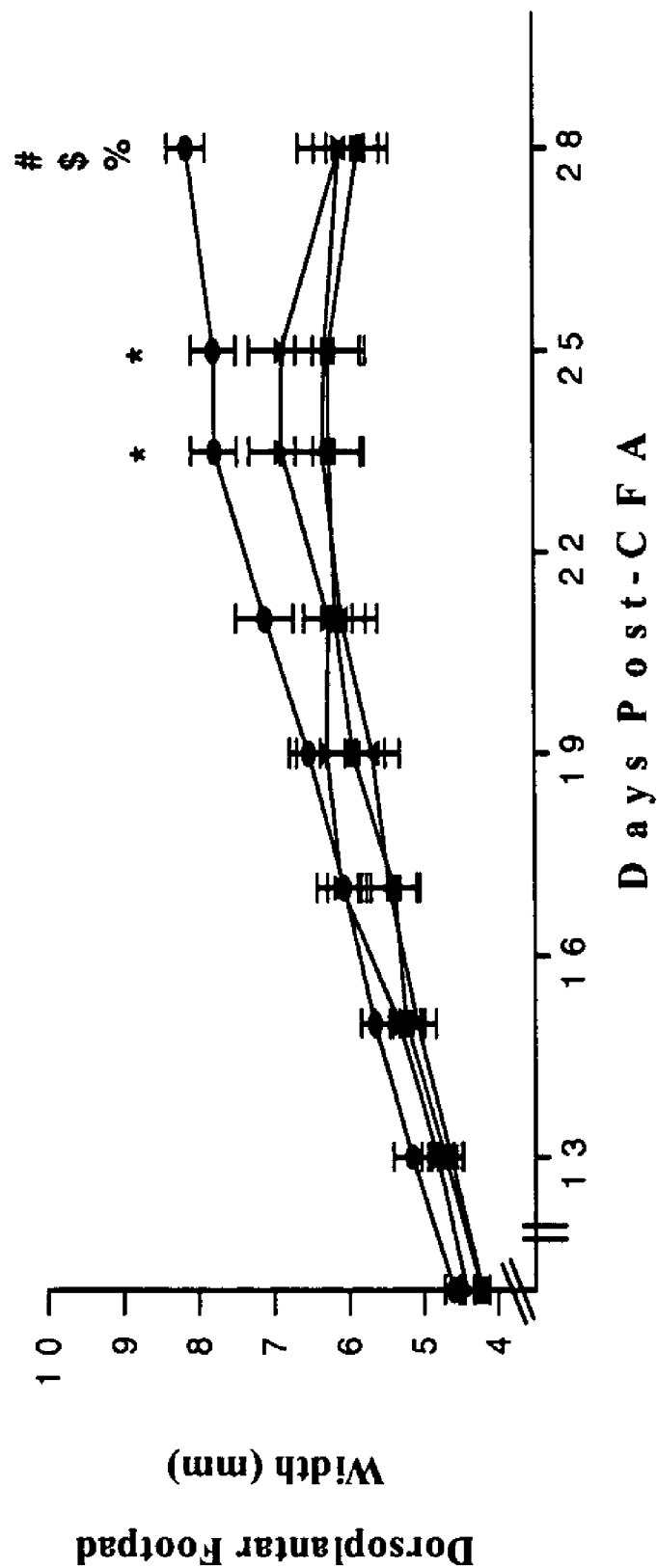

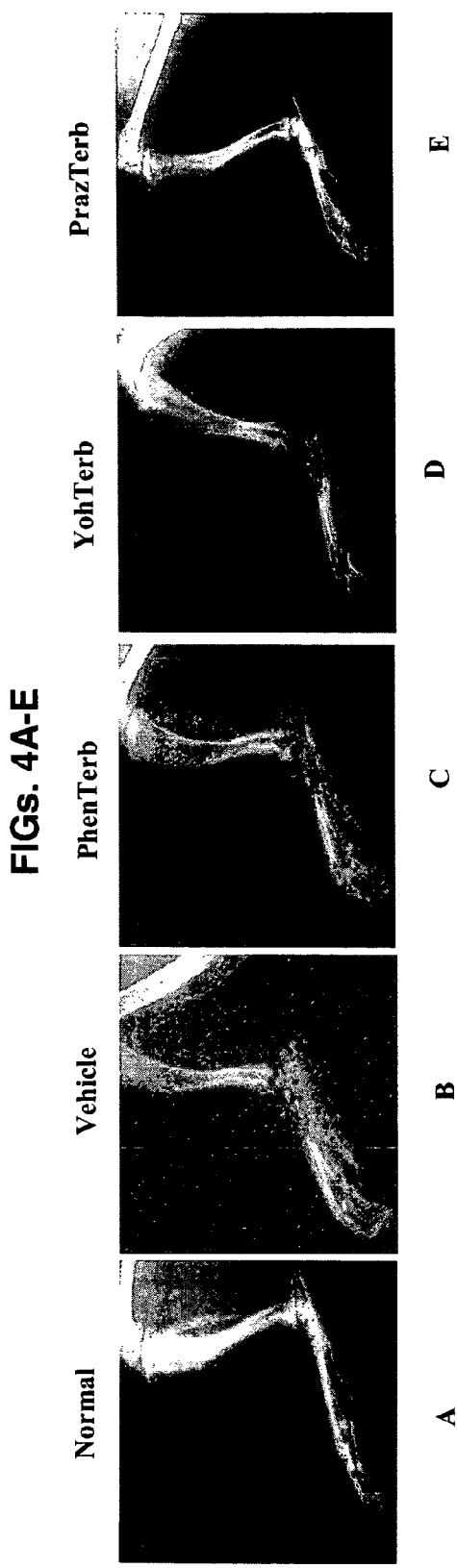
FIGs. 4A-E
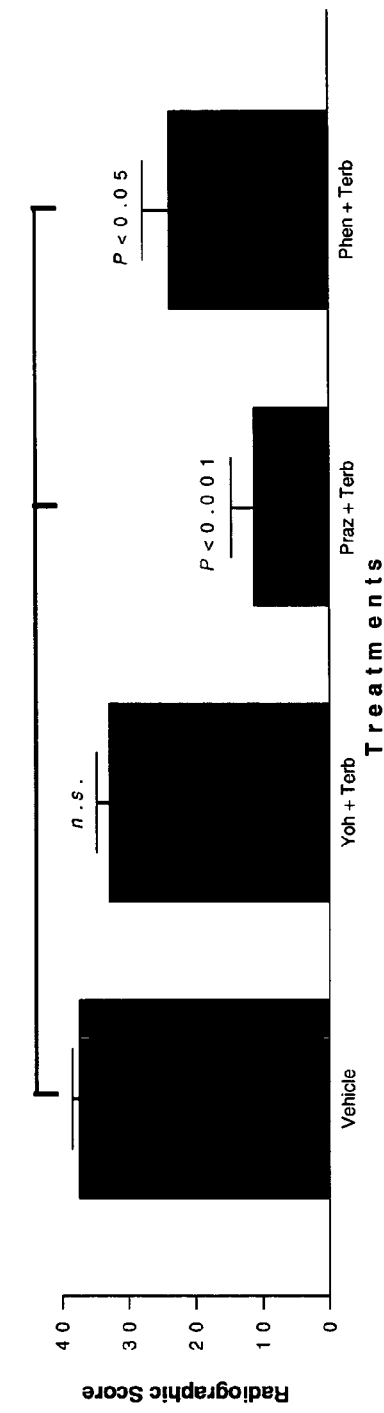
FIG. 4F

TREATMENT OF INFLAMMATORY AUTOIMMUNE DISEASES WITH ALPHA-ADRENERGIC ANTAGONISTS AND BETA-ADRENERGIC AGONISTS

CLAIM TO DOMESTIC PRIORITY

This Application claims the benefit of priority of U.S. Application Ser. No. 60/498,367, filed Aug. 27, 2003.

FIELD OF THE INVENTION

The present invention relates to an improved method for the treatment of inflammatory autoimmune disease, and more specifically to a treatment for inflammatory autoimmune disease, including rheumatoid arthritis, using α-adrenergic antagonists and β-adrenergic agonists in combination.

BACKGROUND OF THE INVENTION

Rheumatoid arthritis (RA) is a chronic inflammatory autoimmune disease of the joints, producing pain and ultimate destruction of the joints. Rheumatoid arthritis is characterized by a chronic inflammatory response in the joint that is directed by macrophages and T cells which invade affected joints. Production of proinflammatory cytokines and other immune cell mediators by these immune cells results in the development of a proliferative invasive connective tissue derived from the synovial membrane and its microvasculature that slowly erodes away the cartilage and bone tissues of joints.

While destruction of joint tissue is the most common feature of RA, the disease can exhibit significant extra-articular manifestations, including cutaneous lesions, vasculitis, blood abnormalities, peripheral neuropathy, pericarditis, arteritis of the viscera, and pulmonary disease. This indicates that RA is a systemic disease that affects the connective tissues of major organs systems. The specific etiology of RA remains elusive. Dysregulation of both cell-mediated and humoral immunity are associated with RA. The pathophysiology of RA intimately involves defects in immune cell regulation. Although the exact mechanisms have not been delineated, the functional activities of macrophages, B cells and T cells from both the joint and lymphoid tissue are affected.

Unfortunately, current treatment strategies for RA and other inflammatory autoimmune diseases are relatively ineffective in preventing bone destruction. Conventional antirheumatic drugs are classified into anti-inflammatory drugs, slow-acting drugs and corticosteroids. Only the slow-acting drugs are thought to be capable of modifying the disease course of rheumatoid arthritis and are referred to as disease modifying anti-rheumatic drugs (DMARD). Drugs from each of these classes are currently being used for treatment of rheumatic diseases. Of these, the central focus has been and remains the DMARDS and nonsteroidal anti-inflammatory drugs (NSAID). NSAIDs effectively abolish the signs and symptoms of joint inflammation and reduce pain. They are not effective in preventing bone and cartilage loss. The value of NSAIDs for treating rheumatic diseases is limited by their side effects.

Aggressive rheumatoid arthritis or early onset of joint destruction indicates the need for rapid treatment with DMARDs. Use of one second-line drug followed by another once the drug being used is no longer effective or is not tolerated well by the patient, is most widely practiced by rheumatologists. Methotrexate and other immunosuppressive drugs, such as cyclosporin and leflunomide were major advancements of the 1980s in treating rheumatoid arthritis. Methotrexate is currently the gold standard for treatment of aggressive rheumatoid arthritis. However, its effectiveness wanes over time and can cause troublesome side effects, including liver damage, sepsis, severe anemia and bleeding.

The approved immunosuppressive drug, leflunomide, was introduced for treating rheumatoid arthritis. This drug relieves joint tenderness and swelling, decreases joint pain and reduces indicators of global disease activity. While leflunomide does not make patients more susceptible to infections, it can cause hair loss, weight loss, hypertension, dizziness, and gastrointestinal side effects. Advances in management of rheumatoid arthritis include the use of corticosteroids as anti-inflammatory and immunosuppressive agents. The main disadvantage of corticosteroids is that long-term use is limited due to adverse effects including weight gain, hyperglycemia, cataracts, osteoporosis, and stomach ulcers.

Thus, treatment for patients with rheumatoid arthritis is imperfect. Accordingly, there is an urgent need for treatments which have few if any side effects and that will be effective in suppressing not only the inflammation but also prevent the bone and cartilage degeneration associated with rheumatoid arthritis.

SUMMARY OF THE INVENTION

The present invention discloses a method for the treatment of inflammatory autoimmune diseases by administering β-adrenergic agonists in combination with α-adrenergic antagonists. The present invention further discloses a compound useful in treating inflammatory autoimmune diseases comprising β-adrenergic agonists in combination with α-adrenergic antagonists.

In certain embodiments, the present invention concerns a compound and method for treating rheumatoid arthritis or other autoimmune diseases, such as inflammatory bowel disease, Krohn's disease, thyroiditis, fibromyalgia, systematic erythermatus, lupus, chronic fatigue syndrome, and Type 1 diabetes, by the application of a therapeutically effective dose of a β-adrenergic agonist, preferably a $\beta_2$-adrenergic agonist such as terbutaline, coupled with a therapeutically effective dose of an α-adrenergic antagonist, preferably α-, $\alpha_1$, and $\alpha_2$-adrenergic receptor subtypes such as phentolamine, prazosin or yohimbine, to human subjects with the disease. Therapeutically effective doses of particular agonists or antagonists and the frequency of dosage administration are to be determined according to protocols understood by those skilled in the art.

Other β-adrenergic agonists useful in this novel method of treatment include: metaproterenol, albuterol, isoetharine, pributerol, bitolterol, ritodrine, and salmeterol. Other α-adrenergic antagonists useful in this novel method of treatment include: yohimbine, regitine, prazosin, doxazosin, tamsulosin, terazosin, octopamine, phenoxybenzamine, phentolamine, hydrochlorothiazide, 5-methyl urapidil, chloroethylclonidine, bunazosin, alfuzosin, RS17053, BMY 7378, urapidil, L-765,314, nicergoline, ABT-866, cyclazosin, A322312, A 119637, fiduxosin, JTH-601, imiloxan, 2 idopropoxyidazoxan, 2-methoxyidazoxan (Rx 821002), idazoxan, piperoxan, BRL 44408, beditin, atipamezole, rawolscine, ARC 239, RS-79948, MK912, RS 79948, UIC 14304 and ethoxyidazoxan.

The β-adrenergic agonists and α-adrenergic antagonists of the present invention may be administered to a patient in a dosage form selected from the group consisting of pills, tablets, capsules, caplets, solutions, suspensions, syrups, suppositories, and aerosols. Additionally, the dosage of the β- (or β$_2$-) and α- (or α$_1$- or α$_2$-) adrenergic agonist and antagonist, respectively, used may be in a sustained-release form. The dosage form of the β-adrenergic agonist and the α-adrenergic antagonists may be administered by various routes including sublingual, oral, intravenous, intramuscularly, rectal, parenteral or subcutaneous.

The β-adrenergic agonists may be administered in various salt forms and may be selected from the group consisting of metaproterenol sulfate; terbutaline sulfate; albuterol sulfate; isoetharine hydrochloride; isoetharine mesylate; pributerol acetate; bitolterol mesylate; or ritodrine hydrochloride; and levalbuterol hydrochloride. The α-adrenergic antagonists also may be administered in various salt forms as well, and may be selected from the group consisting of phentolamine mesylate; regitine mesylate; prasozin; terazosin; doxazosin mesylate; and tamsulosin hydrochloride.

In one embodiment therapeutically effective doses for both the β-adrenergic agonist and α-adrenergic antagonist, respectively, range from about 1.0 to 10.0 mg, with a preferred range of about 2.0 to 5.0 mg, or even more preferably about 1.25 to 2.5 mg. In another embodiment the therapeutically effective dose of the compound is given three times per day depending upon disease severity and patient responses to the drugs. In another embodiment of the present invention method, therapeutically effective dosages of terbutaline from about 1.0 to 10.0 mg coupled with therapeutically effective dosages of phentolamine from about 1.0 to 10.0 mg are administered two or more times per day.

A further embodiment comprises administering a therapeutically effective dose of β-adrengeric agonist followed administering a therapeutically effective dose of an α-adrenergic antagonist, or alternatively, administration of a therapeutically effective dose of β-adrenergic antagonist followed by a therapeutically effective dose of β-adrenergic agonist. Administration of the β-adrenergic agonist and α-adrenergic antagonist can occur within a 24-hour period, a 12-hour period, or preferably an 8-hour period, more preferably an 4-hour period, or most preferably within a one hour period of each other.

BRIEF DESCRIPTION OF THE DRAWINGS

FIGS. 1A-1D shows x-rays demonstrating joint destruction or lack thereof in arthritic animals treated daily with i.p. injections starting at 12 days post adjuvant injection and continuing until day 28 with 1B vehicle, arthritic; 1C phentolamine, arthritic; 1D terbutaline, arthritic; and 1E phentolamine and terbutaline, arthritic. FIG. 1A is an x-ray of a normal non-arthritic rat limb used for comparison.

FIG. 1F shows the radiographic scores for the x-rays in FIGS. 1B-1E.

FIG. 2 is a graph depicting the decreased dorsoplantar swelling by day 28 in animals treated with vehicle, phentolamine and/or trebutaline.

FIGS. 4A-E shows the radiographic analysis of ankle joints treated with vehicle and adrenergic drug combination therapies described in FIG. 3. FIGS. 4A-E is an x-ray of normal non-arthritic rat limbs to be used for comparison. FIG. 4F illustrates the radiographic scores of the animals treated with yohimbine/terbutaline-, phentolamine/terbutaline- and prazosine/terbutaline compared with the vehicle-treated AA rats.

FIG. 5A depicts the changes seen in the white pulp regions both hilar and distal. FIG. 5B depicts changes seen in the red pulp regions of the spleens both hilar and distal.

DETAILED DESCRIPTION

Figure 3:
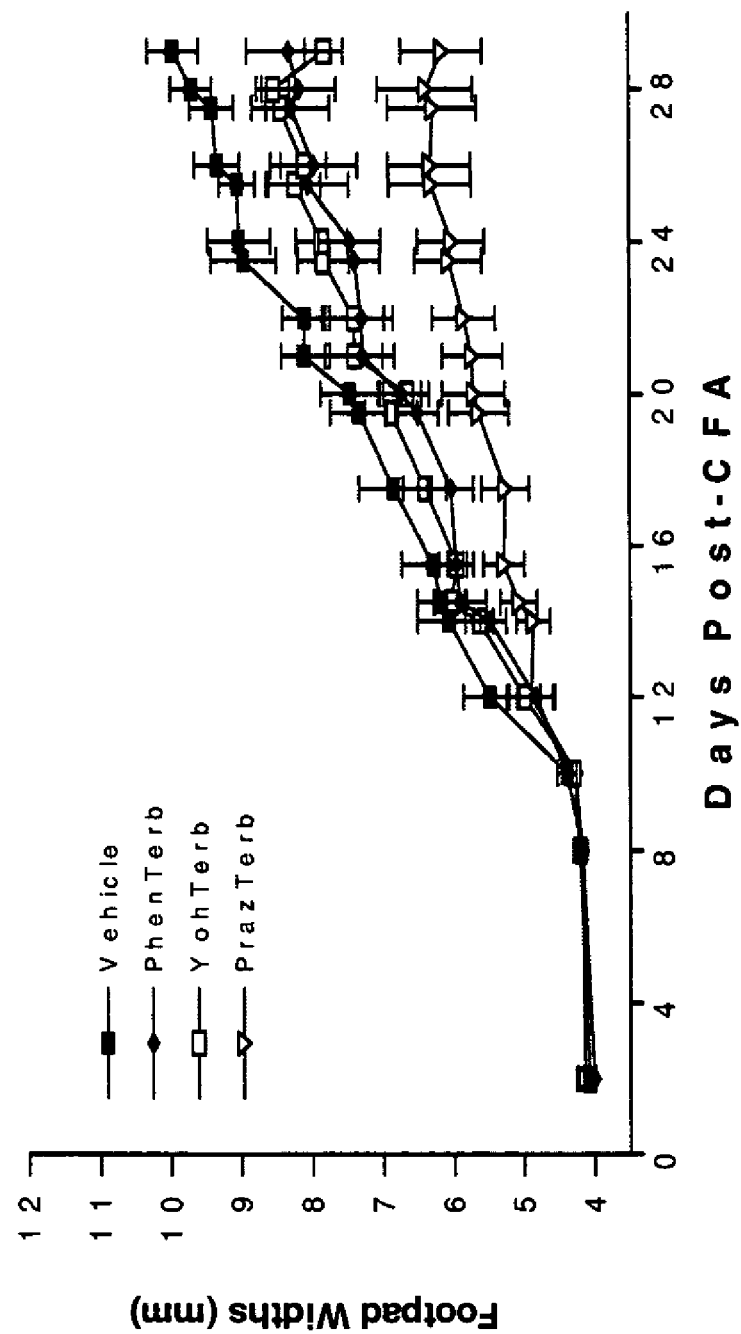
FIG. 3 illustrates the results of continuous treatment with vehicle, combination phentolamine/terbutaline and combination yohimbine/terbutaline or combination prazosine/terbutaline drug therapies from initiated at disease onset, day 12 post-CFA challenge, and continued through day 28, that reduced dorsoplantar footpad widths in arthritic rats when compared with vehicle treated controls.

The present invention addresses one or more short-comings or disadvantages in the available treatment regimens for rheumatoid arthritis or inflammatory autoimmune diseases through the use of a combination of β-adrenergic agonists and α-adrenergic antagonists. In preferred embodiments, the invention contemplates the use of β$_2$-adrenergic agonists and non-specific α- or α$_1$- or α$_2$- adrenergic antagonists, and particularly terbutaline, phentolamine and prazosin, respectively, as agents to treat patients with rheumatoid arthritis (RA) or inflammatory autoimmune diseases.

Cytokine contribution to RA pathology is based largely on shifts in Th1 and Th2 cell cytokine patterns. The nature and concentration of antigen exposure, the degree of antigen-induced activation of subsets of CD4+ T helper (Th) cells (known as Th1 and Th2 cells), and relative production of the different cytokines produced by Th1 and Th2 cells all interact to determine whether an eventual immune reaction is dominated by a cellular or humoral response. Th1 and Th2 subsets in mice and humans determine the cellular or humoral dominance of a response by virtue of the pattern of cytokines that they produce.

Two distinct cytokine secretion patterns have been defined among rodent CD4+ T cells. Type 1 helper (Th1) T cells produce IL-2, gamma interferon (IFNγ, and TNFβ (lymphotoxin) and are important in the generation of delayed-type hypersensitivity (DTH) and cytotoxic responses. In contrast, Th2 cells secrete IL-4, IL-5, IL-6 and IL-10, cytokines that are critical for regulating B cell growth, differentiation, antibody production, and immunoglobulin (Ig) isotype switching. Th1 and Th2 cells are mature T cells derived from a precursor Th0 cell that primarily produces IL-2.

Numerous studies suggest that the balance of cytokines produced by Th1/Th2 T cells play an important role in autoimmune disease development. Modulation of Th1/Th2 cytokine profiles is accepted as having therapeutic value, especially in diseases such as RA, where a specific causative agent has not been identified. Bypassing the causative agent and acting on the cytokine balance of Th1/Th2 cytokines might be a way to control autoimmunity and chronic inflammation.

Cytokines produced by one Th cell subset can modulate the synthesis of cytokines produced by the other subsets. IFNγ produced by antigen-stimulated Th1 cells can inhibit the expansion of Th2 lymphocytes. This, in turn, has been shown to influence the secretion of IgG2a. In contrast, IL-4 and IL-10 produced by Th2 cells can inhibit growth of Th1 cells and production of Th1-type cytokines. Thus, DTH and antibody responses are regulated directly and indirectly by cytokines produced by both Th1 and Th2 cells.

In addition to antigen processing and presenting functions and their role in inflammation, macrophages are also important regulators of cellular and humoral immune responsiveness. Macrophages regulate T cell proliferation in a cell-cell contact manner and, through monokine synthesis and release, play a critical role in driving Th1 and Th2 immune responses.

Th1 cells are the predominate T cell subset in RA joints, however, their function may be limited by other cytokines produced by macrophages in the synovium. A dominant role for activated macrophages in RA disease pathology is gaining acceptance. Altered macrophage function occurs in Adjuvant Arthritis (AA) and RA, and is contributory to defective T and B cell activity. Monocytes are a major source of cytokines in the synovial fluid in RA, particularly the proinflammatory mediators, IL-1 and TNFα. In addition, IL-15, a cytokine with a secondary structure and functional properties similar to IL-2, is produced by macrophages in the RA joint. In the joint, IL-15 is chemotactic, promoting immune cells into the joint, and then stimulating T cell proliferation. Elevated IL-12 concentrations in the RA synovial fluid also are derived from macrophages. These cytokines should promote Th1 responses in the joint, including IFNγ production by local Th1 cells.

Macrophages that invade the joints in the chronic disease phase originate from the bone marrow and lymphoid tissues and are found in close proximity to T cell clusters that resemble the lymphoid aggregates in joints. These macrophage subsets are activated based on expression of class II MHC antigens, high levels of macrophage mediators of tissue destruction, inflammatory cytokines in the joint, and enhanced phagocytic and tumoricidal activity. Activated macrophages also are present in lymphoid tissues in RA animal models.

In collagen- and AA, TNFα mRNA is elevated in lymph nodes (LN) before the onset of arthritis, as well as IFNγ, a Th1 cytokine. Thus, TNFα may prime disease relevant T cells present in LN. In TNFα transgenic mice, elevated TNFα levels produces a chronic erosive arthritis. Likewise, elevated circulating TNFα levels occur with acute flares of RA, supporting an extra-articular source of TNFα that is important in disease development. In contrast, IL-1 is more critically involved in local joint inflammation, since its elevation in the synovium parallels the onset of synovitis, and intra-articular injection of IL-1β induces synovitis.

Treatments aimed at either down-regulating mononuclear phagocyte function or destruction of activated macrophages markedly improved RA in clinical trials. Neutralizing antibodies against TNFα given systemically reduce clinical and histopathologic signs of both collagen- and AA. In TNFα transgenic mice, this same treatment combined with anti-IL-1 receptor therapy prevents the development of arthritis.

Further, administration of cytokines that down-regulate macrophage function, IL-4 or IL-13, reduces joint inflammation and destruction. In streptococcal cell wall-induced arthritis, systemic treatment with IL-4 reduced inflammation and joint destruction by inhibiting IL-1 and TNFα, and enhancing IL-1Ra. Conversely, neutralization of IL-10 promoted macrophage-mediated joint pathology in collagen-induced arthritis. In animals with fully expressed AA, treatment with bisphosphonate clodronate, a toxin taken up into liposomal vesicles by macrophages and that subsequently destroys them, significantly reduced joint inflammation and destruction, giving this drug 'disease-modifying' status, with long-lasting effects after short-term therapy.

Long-term loss of macrophages in lymphoid organs correlated with the anti-arthritic effects. In fact, clodronate targeted macrophages in secondary lymphoid organs, rather then affected joints. ED3+ macrophages, important for cell-cell interactions with T cells, were preferentially depleted in spleen and LN. In contrast, clodronate treatment was only marginally effective when administered into affected joints. Additionally, repeated leukapheresis effectively depleted circulating monocytes in RA patients with consequent reduction in disease symptoms. Thus, macrophages play a central role in sustaining arthritis and demonstrate the critical role for systemic monocytes and macrophages and their secreted cytokines in RA pathology.

The Central Nervous System (CNS) plays a role in controlling levels of cytokines and the activation of different T cell subsets is well documented. The Sympathetic Nervous System (SNS), through innervation of lymphoid tissues, provides a direct route for communication between the nervous and immune systems. This innervation is regional and specific, distributing along the vasculature and in the parenchyma adjacent to immune cells. Adrenergic receptors are present on a variety of immune cells, including T and B lymphocytes, and macrophages, and stimulation of these receptors can alter immune responses.

$Beta_2$-adrenergic receptors are selectively expressed by Th1, but not by Th2, cell clones. In functional studies, Th1 and Th2 cells are differentially regulated by β-AR stimulation. Th1 clones treated with terbutaline, a $β_2$-adrenergic receptor agonist, before activation with enriched populations of antigen-specific B cells or anti-CD3 antibodies, inhibits both IL-2 and IFNγ production by Th1 cell clones, but does not affect IL-4 or IL-10 production by Th2 cell clones. Additionally, terbutaline application reduced IL-2-dependent T cell proliferation consistent with the terbutaline-induced reduction in IL-2 production. Collectively, these findings suggest differential regulation of Th cell subset clones. Thus, in vivo, 32-adrenergic receptors distinguish Th1 and Th2 cells. Therefore, the differential $β_2$-adrenergic receptor expression by Th1 and Th2 cells provides a mechanism for modulating clonal expansion of activated Th cells by sympathetic nerves.

Functionally, $β_2$-adrenergic receptor stimulation of activated Th cell clones affects their ability to help B cells produce specific antibody isotypes. Terbutaline application to Th cells before activation inhibited IgG2a (but not IgG1) production when cultured with B cell clones, blockable by addition of nadolol (β-adrenergic receptor antagonist) or by exogenous administration of IFNγ. Further, after B cells and Th cells are activated by exposure to a Th cell-dependent antigen in vitro, $β_2$-adrenergic receptor agonists enhance antibody production by B cells, due to enhanced B cell proliferation and differentiation into antibody-secreting cells.

The effect of $β_2$-adrenergic receptor stimulation on B cell function results from a direct effect of AR agonists on B cells. Thus, $β_2$-adrenergic receptor stimulation enhances B cell function and that under conditions of enhanced sympathetic tone, i.e. stress, prior to immune activation, both Th1 and B cell function will be diminished. In contrast, if sympathetic outflow is enhanced, NE has a permissive effect on humoral immunity.

The effect of chemical sympathectomy (SympX) with 6-OHDA on cytokine and antibody production after keyhole limpet hemocyanin (KLH) immunization was examined in young adult mice with different Th dominance (e.g., BALB/cJ mice with a predominant Th2 cytokine profile, and C57Bl/6 mice with a predominant Th1 cytokine profile). SympX enhanced KLH-stimulated IL-2 and IFNγ production by splenocytes in vitro, in both murine strains. Under the same conditions, IL-4 also is elevated in splenocyte cultures with cells from each strain producing more of its dominant cytokine. Anti-KLH antibody titers for IgG1, IgG2a, and IgM were elevated in serum from immunized, denervated C57Bl/6, but not BALB/c mice. This is consistent with a tonic inhibitory mechanism of immune regulation by the SNS, and differential responsiveness by the two strains.

The SNS plays a modulatory role to maintain immune system homeostasis, however, few studies have examined whether the SNS is playing a significant role in autoimmune diseases, such as RA, where immune system homeostasis is disrupted. Impaired sympathetic nervous system function has been extensively described in RA using cardiovascular tests during orthostatic stress, the valsalva maneuver, deep breathing, pupil size and perspiration. These changes are associated with increased urinary metabolites of NE, suggesting an increase in sympathetic outflow. Defective function of SNS in patients with RA may contribute to immune derangement and severity of illness. In an AA rat model, 7 days after injection of adjuvant and preceding the onset of inflammation, corticotrophin releasing hormones (CRH) mRNA were increased in the PVN significantly above controls following immobilization stress. In contrast, CRH mRNA levels in the PVN were significantly lower than in controls 14 days after adjuvant injection. This indicates a CRH induced increase in sympathetic outflow in early disease stages, followed by a decrease in outflow in late AA stages.

Figure 5A:
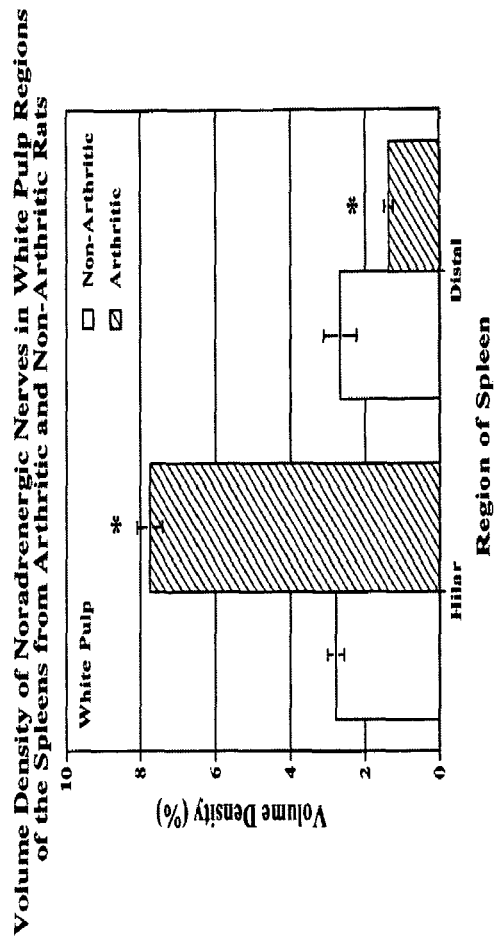
FIGS. 5A-B shows an injury/sprouting response of the NA nerves in the spleens from arthritic and non-arthritic rats.
Figure 5B:
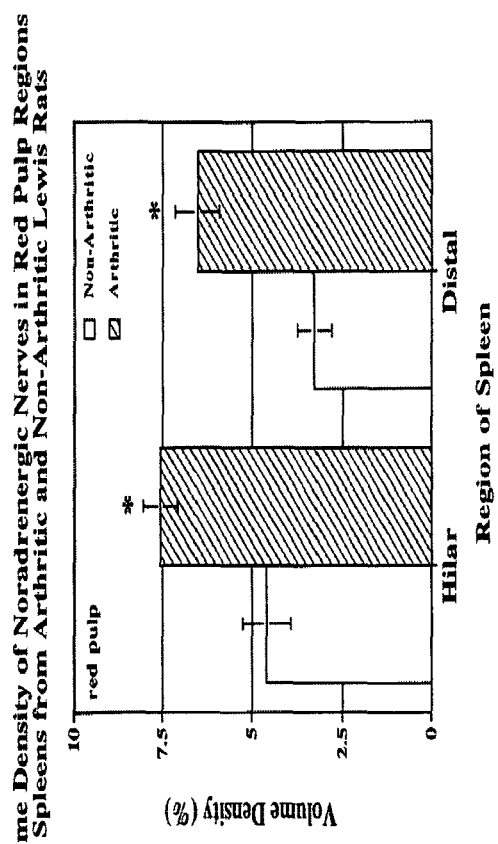

The inventors have documented a sprouting/injury response in late disease stages in lymphoid organs, as well as a decrease in NE concentrations in spleens and LN of AA rats during late stages (FIGS. 5A and 5B). Noradrenergic (NA) innervation in spleens of Lewis rats was examined 28 days following adjuvant treatment to induce arthritis or vehicle for the adjuvant using fluorescence histochemistry for catecholamines with morphametric analysis and immunocytochemistry for thyrosine hydroxylase. In AA rats, sympathetic nerve densityin the hilar regions, where NA nerve fibers enter the spleen, was increased by two-fold over that observed in vehicle treated rats.

In contrast, there was a striking two-fold decline in the density of NA nerves in the splenic regions distal to the hilus in arthritic rats compared with non-arthritic animals. In both treatment groups, NA nerves distributed to the central arterioles, white pulp regions, trabeculae and the capsule. However, NA nerve density in the white pulp was reduced, but was increased in the red pulps in AA rats compared with non-AA rats. These findings indicate an injury/sprouting response with disease development whereby NA nerves die back in distal regions and undergo a compensitory sprouting response in the hilus.

The redistribution of NA nerves from white pulp to red pulp suggests these nerves signal activated immune cells localized to the red pulp in the AA animals. Changes in adrenergic receptor expression, (decreased β-adrenergic receptors on peripheral blood mononuclear cells and increased $\alpha_1$-adrenergic receptors on monocytes) have been reported in RA patients. In the case of $\alpha_1$-adrenergic receptor expression in monocytes from arthritic patients, peripheral blood mononuclear cells of healthy donors did not express functional $\alpha_1$-adrenergic receptors, indicating that disease onset is associated with adrenergic receptor expression not normally expressed by these cells.

Stimulation of $\alpha_1$-adrenergic receptors on peripheral blood leukocytes of RA patients increased production of proinflammatory cytokines. Thus, monocyte $\alpha_1$-adrenergic receptor expression is likely to contribute to the disease. Monocyte $\alpha_1$-adrenergic receptor expression can be induced by treatment with an $\beta_2$-adrenergic receptor agonist, suggesting that $\beta_2$-adrenergic receptor stimulation can regulate monocyte $\alpha_1$-adrenergic receptor expression. Collectively, this indicates a role for SNS modulation of immune function in RA.

The effects of β-adrenergic agonists on immune function results from binding of these ligands to β-adrenergic receptors expressed on lymphocytes and macrophages/monocytes to induce activation of Gs proteins and elevated levels of intracellular cAMP. Cyclic AMP induces downstream signal modifications that dampen immune cell responses. Elevation of intracellular cAMP activates protein kinase A (PKA0, which is followed by interfering with activation of Ras proteins). PKA interferes with Raf-1 binding to Ras, thus inhibiting downstream signaling of immune responses.

Additionally, $\beta_2$-adrenergic receptors can switch their coupling from Gs proteins to Gi proteins, an effect that is also mediated by PKA. PKA phosphorylation of the $\beta_2$-adrenergic receptor leads to $\beta_2$-adrenergic receptor desensitization, reduction cAMP production in response to further stimulation, and causes the inhibition of the Gs mediated adenylyl cyclase signal that started the process. Coupling of the $\beta_2$-adrenergic receptor to Gi proteins then initiates a second wave of Gi-mediated signaling to activate mitogen activated protein (MAP) kinase pathways and promote functional responses initiated by stimulators of immune responses.

The effects of non-specific and specific α-adrenergic antagonists on immune function have been studied less. Binding of an α-adrenergic agonist to $\alpha_2$-adrenergic receptors expressed by immune cells results in activation of Gi proteins. Activation of these G proteins results in activation of MAP kinases in a Ras-dependent manner that is independent of phospholipase activation or adenylyl cyclase. Stimulation of the $\alpha_2$-adrenergic receptor induces phosphorylation of shc by the Gi βλ subunit. Shc is one of three docking proteins, which function as platforms for assembly of a Ras activation complex. Thus, $\alpha_2$-adrenergic receptors can modulate immune responses by impacting MAP kinase downstream signaling pathways of immune cells at the levels of Ras.

Binding of an α-adrenergic agonist to $\alpha_1$-adrenergic receptors expressed by immune cells results in activation of pertussis toxin-insensitive Gq/11 proteins. Activation of these G proteins leads to activation of an intracellular signal transduction pathway known to stimulate phospholipase C (PLC) and diacyl glycerol (DAG) and inositol triphosphate 3 (IP3) generation. This is followed by IP3 dependent increases in intracellular calcium and activation of protein kinase C (PKC) by DAG. Activation of PKC results in activation of mitogen-activated protein (MAP) kinase activation. Activation of $\alpha_1$-adrenergic receptors thus can impact immune function by modulating MAP kinase pathways known to be involved as intracellular signal cascade pathways for induction of immune responses. Activation of the $\alpha_1$-adrenergic receptor can also impact immune functions by stimulation of nuclear factor of activated T cells (NF-AT) transcription factors.

At a functional level, drugs acting on adrenergic receptors expressed by lymphocytes and monocytes could impact rheumatoid arthritis by at least two different mechanisms, by altering cytokine production or blocking macrophage functions. As indicated above, shifting cytokine profiles of Th cells towards Th2 cells significantly reduces disease severity. Similarly, drugs that inhibit macrophage functions or neutralize TNFα have a profound beneficial effect in reducing disease severity. Stimulation of the sympathetic nervous system promotes a shift in Th cell cytokines profiles toward a Th2 response, thus inhibiting cell mediated immunity.

In addition, activation of macrophage β-adrenergic receptors inhibits macrophage functions. However, interaction of norepinephrine with macrophage/monocyte $\alpha_1$-adrenergic receptors can stimulate production of TNFα, a key cytokine in promoting inflammation and bone destruction in RA. Presence of an $\alpha_1$-adrenergic antagonist would block this macrophage response.

Further, NA innervation of secondary immune organs is lost as a part of the disease pathology. This results in a loss of a negative feedback system required for dampening immune and inflammatory responses during the acute and chronic disease stages. This feedback system normally is responsible for maintaining homeostasis of the immune system and may be critical for returning immune system functions back to normal levels in RA.

Therefore, the present invention discloses β-adrenergic agonists in combination with α-adrenergic antagonists that are useful in treating rheumatoid arthritis, as these drugs are effective in treating adjuvant-induced arthritis, an animal model of rheumatoid arthritis. In certain embodiments, the present invention concerns a method for treating rheumatoid arthritis or autoimmune diseases by the application of a therapeutically effective dose of a β-adrenergic agonist, and preferably a $β_2$-adrenergic agonist such as terbutaline, coupled with a therapeutically effective dose of an α-, $α_1$- or $α_2$-adrenergic antagonist, and preferably phentolamine, prazosin or yohimbine, to human subjects with the disease.

As used herein, the term "treating a disease by the application of a therapeutically effective dose of a β-adrenergic agonist" and "a therapeutically effective does of an α-, $α_1$- or $β_2$-adrenergic antagonist" is used to signify that the β-adrenergic agonist and α-adrenergic antagonist is supplied to the patient in amounts, and for a period of time, that are effective to provide improvement in one or more of the clinically measured parameters of the disease, particularly disease parameters of cartilage and bone destruction.

Several inflammatory autoimmune diseases are proposed to be treatable by combined β-adrenergic agonists and α-adrenergic antagonists of the present invention, such as inflammatory bowel disease, Krohn's disease, fibromyalgia, lupus, chronic fatigue syndrome, and Type 1 diabetes. The efficacy of the disclosed treatment is based on common mechanisms of immune dysfunction, inflammation targeting specific organs in these diseases and the fact that a dying back of sympathetic nervous system nerve fibers supplying immune organs have been documented in each of these disorders.

To determine whether there has been an improvement in one or more of the clinically measured parameters of the disease, one would determine the value of such a parameter in a given patient both before and during treatment. Various clinical signs and symptoms are known by those known to be skilled in the art as suitable markers of disease severity. Symptoms of inflammatory joint disease (compared with mechanical problems) should be assessed to gain evidence of active disease. These include degree of joint pain, duration of morning stiffness, severity of fatigue, presence of actively inflamed joints on examination, and limitation of function.

However, the joint examination may not adequately reflect disease activity and structural joint damage. Periodic measurements of erythrocyte sedimentation rate or C-reactive protein elevation, functional status (loss of motion, instability, malalignment, and/or deformity of affected joints) and radiographic examinations of involved joints should be performed. Functional status assessment can be performed with questionnaires known in the art such as the Arthritis Impact Measurement Scales or the Health Assessment Questionnaire.

The present invention has the advantage of being a novel application and use of agents that are already in use clinically in the treatment of various other disorders and ailments. The adrenergic agents of the present invention are safer and have fewer side effects than drugs currently being used to treat rheumatoid arthritis and the other autoimmune diseases listed. Accordingly, some $β_2$-adrenergic agonists considered to be of use in the present invention include metaproterenol, albuterol, isoetharine, pirbuterol, bitoltrol, ritodrine, or salbutamol, and preferably, terbutaline.

Some of the α-adrenergic antagonists considered to be of use in the present invention include yohimbine, regitine, prazosin, doxazosin, tamsulosin, terazosin, octopamine, phenoxybenzamine, phentolamine, hydrochlorothiazide, 5-methyl urapidil, chloroethylclonidine, bunazosin, alfuzosin, RS17053, BMY 7378, urapidil, L-765,314, nicergoline, ABT-866, cyclazosin, A322312, A 119637, fiduxosin, JTH-601, imiloxan, 2 idopropoxyidazoxan, 2-methoxyidazoxan (Rx 821002), idazoxan, piperoxan, BRL 44408, beditin, atipamezole, rawolscine, ARC 239, RS-79948, MK912, RS 79948, UIC 14304 and ethoxyidazoxan.

The β-agonists and α-antagonists may be administered to the patient in any pharmaceutically acceptable vehicle and by any route heretofore acceptable for these agents. The preferred route of administration is orally, although one may, if desired, choose to administer the agonists or antagonists intravenously, sublingually, intramuscularly, subcutaneously, or in a sustained release form.

As will be understood by those skilled in the art, the effective doses of the 13-agonist and α-antagonist will depend upon the route of administration and the patient's sensitivity to the particular β- (or $β_2$-) adrenergic agonist and α- (or $α_1$- or $α_2$-) adrenergic antagonist. Recommended doses for both the β-adrenergic agonist and α-adrenergic antagonist, respectively, range from about 1.0 to 10.0 mg, with a preferred range of about 2.0 to 5.0 mg, or even more preferably about 1.25 to 2.5 mg given three times per day depending upon disease severity and patient responses to the drugs. The dosages may be more effectively adjusted on an individual basis as the disease severity varies from patient to patient.

This invention comprises a novel method for the treatment of patients diagnosed as having a rheumatoid arthritis or inflammatory autoimmune disease with a combined use of a β-adrenergic agonist (preferably a $α_2$-adrenergic agonist) and an α-adrenergic antagonist (preferably an $α_1$- or $α_2$-adrenergic antagonist). This method comprises the administration of an effective dose of a β-adrenergic agonist (preferably a $β_2$-adrenergic agonist) and an α-adrenergic antagonist (preferably a $α_1$- or $α_2$-adrenergic antagonist) to patients diagnosed as having rheumatoid arthritis or other inflammatory autoimmune disease. Even more particularly, the method of the present invention comprises the administration of an effective dose of the $β_2$-adrenergic agonist terbutaline coupled with and effective dose of the α-adrenergic antagonist, phentolamine (or more specifically $α_1$- or $α_2$-adrenergic antagonists) to patients with rheumatoid arthritis or other inflammatory autoimmune disease.

Terbutaline is known to be an agent of use as a bronchodilator for treating or controlling acute or chronic bronchial asthma, exercise-induced bronchospasm, bronchitis, emphysema, bronchiectasis or other obstructive pulmonary diseases, as well as a uterine relaxant in premature labor. Treatment with β- or $β_2$-adrenergic agonists reduce disease severity of demyelinating autoimmune diseases, including multiple sclerosis, myasthenia gravis, demyelinating polyradiculoneuropathy, experimental allergic neuritis, and post-infectious encephalomyelitis. For example, salbutamol, a $β_2$-adrenergic agonist, reduces the severity of collagen-induced arthritis, an animal model of rheumatoid arthritis.

Phentolamine is known to be an agent of use in prevention or control of hypertensive episodes that may occur in a patient with pheochromocytoma as a result of stress or manipulation during preoperative preparation and surgical excision. Its use has been indicated for prevention and treatment of dermal necrosis and sloughing following IV administration or extravasation of norepinephrine or dopamine as well. Phentolamine has been used to treat hypertensive crises secondary to MAO inhibitor/sympathomimetic amine interactions and rebound hypertension on withdrawal of clonidine, propranolol or other antihypertensives. It has also been used in combination with papaverine as an intracavernous injection for impotence. Alpha$_1$-adrenergic antagonists are used for the treatment of hypertension, benign prostatic hyperplasia, refractory chronic heart failure and management of raynaud's vasospasm. However, no adequate information exists on the use of α-adrenergic antagonists in arthritic patients.

To date, there has been no disclosure as to the combined use of a β-adrenergic agonist and a α-adrenergic antagonist (regardless of the receptor subtype) in the treatment of rheumatoid arthritis or inflammatory autoimmune diseases. The present invention discloses that a combination of both these drugs is effective in the treatment of such disorders, and particularly, in the treatment of rheumatoid arthritis. Other β$_2$-adrenergic agonists useful in this novel method of treatment include: metaproterenol, albuterol, isoetharine, pributerol, bitolterol, ritodrine, and salmeterol. Other α-adrenergic antagonists useful in this novel method of treatment include: yohimbine, regitine, prazosin, doxazosin, tamsulosin, terazosin, octopamine, phenoxybenzamine, phentolamine, hydrochlorothiazide, 5-methyl urapidil, chloroethylclonidine, bunazosin, alfuzosin, RS17053, BMY 7378, urapidil, L-765,314, nicergoline, ABT-866, cyclazosin, A322312, A 119637, fiduxosin, JTH-601, imiloxan, 2 idopropoxyidazoxan, 2-methoxyidazoxan (Rx 821002), idazoxan, piperoxan, BRL 44408, beditin, atipamezole, rawolscine, ARC 239, RS-79948, MK912, RS 79948, UIC 14304 and ethoxyidazoxan.

The β-adrenergic agonists and α-adrenergic antagonists of the present invention may be administered to a patient in a dosage form selected from the group consisting of pills, tablets, capsules, caplets, solutions, suspensions, syrups, suppositories, and aerosols. Additionally, the dosage of the β- (or β$_2$-) and α- (or α$_1$- or α2-) adrenergic agonist and antagonist, respectively, used may be in a sustained-release form to cause the action of such agonists and antagonists to persist over a more prolonged period of time. Such sustained-release formulations are well known to those skilled in the art.

The β-adrenergic agonists may be administered in various salt forms. For example, the following are commercially available: metaproterenol sulfate as "Alupent" (Boehringer Ingelheim) or "Metaprel" (Dorsey); terbutaline sulfate as "brethaire" or "Brethine" (Ciba-Geigy) or "Bricanyl" (Merrell-Dow); albuterol sulfate as "Proventil" (Schering-Plough) or "Ventolin" (Glaxo); isoetharine hydrochloride as "Bronkosol" (Sterling) (Parke-Davis) or isoetharine mesylate as "Bronkometer" (Sterling); pributerol acetate as "Max-air"; bitolterol mesylate as "Tomalate" (Sterling); or ritodrine hydrochloride as "Pre-Par" (Philips-Duphar) or "Yutopar" (Astra); levalbuterol HCl as "Xopenex" (Sepracor); Salmeterol as "Serevent" (GlaxoWellcome) or "Serevent Diskus" (GlaxoWellcome).

The α-adrenergic antagonists also may be administered in various salt forms as well. For example, the following are commercially available: Phentolamine mesylate (Bedford); Regitine mesylate (Ciba); prasozin as "Prasozin" (Geneva, Goldline, Lederle, Major, Moor, Rugby, Schein, Squibb, Zenith) or "Minipress" (Pfizer); terazosin as "Hytrin" (Abbott); doxazosin mesylate as "Cardura" (Roerig); and tamsulosin hydrochloride as "Flomax" (Boehringer Ingleheim).

The dosage form of the β-adrenergic agonist and the α-adrenergic antagonists may be administered by various routes including sublingual, oral, intravenous, rectal, parenteral or subcutaneous. Therapeutically effective doses of particular agonists or antagonists and the frequency of dosage administration are to be determined according to protocols understood by those skilled in the art. In one embodiment of the present invention method, therapeutically effective dosages of terbutaline from about 1.0 to 10.0 mg coupled with therapeutically effective dosages of phentolamine from about 1.0 to 10.0 mg are administered two or more times per day.

The treatment may also comprise administering a therapeutically effective dose of β-adrengeric agonist followed administering a therapeutically effective dose of an α-adrenergic antagonist, or alternatively, administration of a therapeutically effective dose of α-adrengeric antagonist followed by a therapeutically effective dose of β-adrenergic agonist. Administration of the β-adrenergic agonist and α-adrenergic antagonist can occur within a 24-hour period, a 12-hour period, or preferably an 8-hour period, more preferably an 4-hour period, or most preferably within a one hour period of each other.

The exact mechanism by which the β- (or β$_2$-) adrenergic agonist and α- (or α$_1$- or γ$_2$-) adrenergic agonists and antagonists, respectively, exert a suppressive effect on disease severity of rheumatoid arthritis or inflammatory autoimmune diseases (e.g., inflammatory bowel disease, Type 1 diabetes, lupus, and Krohn's disease) is unknown. However, this present disclosure shows that there is an increase in sympathetic outflow early in the disease that later results in a loss of sympathetic nerve fibers that normally signal immune cells in secondary lymphoid tissue. These nerve fibers are necessary for maintaining immune system homeostasis.

Beta-agonists replace the function of the lost sympathetic nerve fibers that occurs as the disease progresses. Stimulation of the sympathetic nervous system is known to promote or inhibit production of specific cytokines by macrophages and/or T helper lymphocytes that shift the immune response towards humoral immunity. When this innervation to secondary lymphoid immune organs is lost, the effect is to promote or inhibit production of specific cytokine by macrophages and/or T helper lymphocytes that shift the immune response towards cell mediated immunity, and in arthritic patients, increased disease severity. The β-adrenergic agonist would be expected to shift cytokine production by immune cells toward a profile that favors humoral immunity.

The function of the α-adrenergic antagonist is to block stimulation of activated macrophage α-adrenergic receptors by circulating catecholamines, either norepinephrine or epinephrine, that promote production of proinflammatory mediators important in disease progression. The present disclosure demonstrates that early in the disease process there is an increase in sympathetic outflow that results in a large increase in release of norepinephrine from nerves targeting immune cells.

Stimulation of β-adrenergic receptors by this adrenergic agonist is known to stimulate expression of α-adrenergic receptor expression by monocytes/macrophages. Activation of α-adrenergic receptors by circulating norepinephrine or epinephrine, or following β-agonist drug treatments, promotes production of proinflammatory mediators by these macrophages, including tumor necrosis factor α. The addition of the α-adrenergic antagonist in this invention is proposed to block the induction of proinflammatory mediators by activated macrophages. This is supported by reports that α$_1$-adrenergic receptors are expressed on monocytes from arthritic patients but not expressed on monocytes from healthy donors, indicating that disease onset is associated with α-adrenergic receptor expression not normally expressed by these cells.

Stimulation of α$_1$-adrenergic receptors on peripheral blood monocytes of rheumatoid arthritis patients increased production of proinflammatory cytokines. Further, monocyte α$_1$-adrenergic receptor expression can be induced by treatment with a $\beta_2$-adrenergic agonist, suggesting that $\beta$-adrenergic receptor stimulation can regulate monocyte $\alpha_1$-adrenergic receptor expression.

In this manner, $\beta_2$-adrenergic agonists coupled with $\alpha$-adrenergic antagonists are believed to be likely to provide a similar suppressive effect on the excessive immune responses found in other inflammatory autoimmune diseases. By inhibiting cell mediated immunity through shifting T helper lymphocyte production of cytokines that promote humoral immunity, in the case of the $\beta$-adrenergic agonist, and inhibiting production of proinflammatory mediators by macrophages, in the case of the $\alpha$-adrenergic antagonists, these agonists and antagonists are believed to be likely to provide a similar suppressive effect on the excessive cell mediated immune responses found in other inflammatory autoimmune diseases. Thus, the $\beta_2$-adrenergic agonists and $\alpha$-adrenergic antagonists of the present treatment method may be useful in treating other inflammatory autoimmune diseases, such as inflammatory bowel disease.

The following example is included to demonstrate preferred embodiments of the invention. It should be appreciated by those of skill in the art that the techniques disclosed in the example which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Combined $\beta_2$-Adrenergic Agonist (Terbutaline) and $\alpha$-Adrenergic Antagonist Suppression of Adjuvant-Induced Arthritis in Rats 1. Method Lewis rats with AA, a model for RA, were used to examine the combined action of the $\beta_2$-adrenergic receptor agonist terbutaline and the non-specific $\alpha$-AR antagonist phentolamine. AA was induced in adult male Lewis rats (200-225 gm) by a base of the tail intradermal injection of complete Freund's adjuvant (CFA). The CFA (0.03 g dried and heat killed *Mycobacterium butyricum* (Difco, Detroit, Mich.) emulsified in 10 ml sterile mineral oil) was prepared by grinding the *M. butyricum* with a mortar and pestle until the bacterial cell wall turned from a light beige to an eggshell white powder.

The mineral oil was then slowly worked into the bacterial cell wall using the mortar and pestle. The suspension was treated with a sonic dismembraner for 5 minutes to ensure that the bacterial cell wall remained suspended in the mineral oil for animal injections. While there was variability in the severity of disease development between the preparations of adjuvant, there was very little variability within individual batches. All animals in each experiment were challenged with the same preparation of adjuvant and 100% of the animals developed arthritis.

Phentolamine (an $\alpha$-adrenergic receptor antagonist) and terbutaline (a $\beta_2$-adrenergic receptor agonist) were obtained from Sigma Chemical Company (St. Louis, Mo.). Both adrenergic drugs were dissolved in 0.01 mM ascorbic acid in 0.9% sterile, endotoxin-free saline. Adrenergic therapy with phentolamine and/or terbutaline or vehicle was started on day 12 post-immunization, the time of disease onset, and continued until sacrifice. The dose of phentolamine (500 µg/Kg/day) and/or terbutaline (600 µg/day) were administered by intraperitoneal (i.p.) injections twice a day in a total volume of 500 µl per injection.

The inflammatory response in the arthritic rats was assessed by routine methods previously described. Dorsoplantar width of the hind feet were measured using a Mitutoyo Corporation dial thickness gauge, beginning the day of CFA-immunization and continued approximately every other day until sacrifice. The right and left footpads from each animal were averaged together. The individual means for each animal were then averaged within each group and subjected to a repeated measure two-way analysis of variance (ANOVA; P<0.05) with Bonferroni post-hoc testing. The animals were sacrificed when significant differences between the dorsoplantar footpads of the groups became apparent in the late effector phase, 28 days post-adjuvant injection.

Prior to sacrifice the animals were anesthetized with a 1.0 ml i.p.-injection of 8% chloral hydrate in sterile saline and radiographs were taken of their hind limbs to assess disease severity. Radiographs were taken using the following settings: 400 nN, 50 kvp, 0.4 second exposure time, at 40 centimeters and X-OMAT processor. X-rays were evaluated using a grading scale modified from Ackerman and coworkers.

In short, the radiographs were coded to obscure the treatment groups, and then two independent observers subjectively rated each of the radiographs on the scale: 0 (normal), 1 (slight), 2 (mild), 3 (moderate), and 4 (severe) abnormalities in the tissue. The radiographs were scored for each of the following characteristics: (1) swelling as indicated by the width of soft tissue shadows and alterations in the normal configuration of the soft tissue planes; (2) osteoporosis as measured by bone density (recognized by increases in radiolucency relative to uninvolved adjacent bone); (3) cartilage loss shown by narrowing of the joint spaces; and (4) heterotopic ossification defined as proliferation of new bone tissue (fine ossified line paralleling normal bone but not contiguous with calcified area of the bone itself).

The radiographic scores for each category were added for both hind limbs giving a maximum score of 40, and the individual scores for each animal were then averaged within the treatment groups and expressed as a mean±standard error of the mean (SEM), and subjected to Kruskal-Wallis statistical analysis (non-parametric statistic equivalent to an ANOVA; p<0.05) followed by Dunn post-hoc testing. This experiment was replicated twice. Protocols for the use and care of the animals in the study were approved prior to beginning the experiments by the Sun Health Research Institute Animal Use and Care Committee and complied with NIH guidelines for the humane use and care of research animals.

2. Results

FIG. 2 illustrates that continuous treatment of adrenergic drug therapies from disease onset affected dorsoplantar footpad widths in arthritic rats. All CFA-challenged rats developed AA between days 10-12 (FIG. 2). Soft tissue swelling was significantly decreased in terbutaline- or phentolamine-treated animals compared with the vehicle-treated AA rats by day 28 post-adjuvant injection (Terbutaline: $F_{9,70}$=27.61, Day 28: $t_{Terb}$=5.998, P<0.001) (Phentolamine: $F_{9,70}$=30.50, $t_{Phen}$=3.594, P<0.01) (FIG. 2). Combination phentolamine and terbutaline treatment also significantly reduced the soft tissue swelling in the hind limbs by day 23, an effect which was maintained through day 28 compared with the vehicle-treated arthritic rats (PhenTerb: $F_{9,70}$=30.04, Day 23: $t_{PhenTerb}$=3.363, P<0.05; Day 25: $t_{PhenTerb}$=3.557, P<0.01;

Day 28: $t_{PhenTerb}$=5.300, P<0.001). These findings were replicated twice with similar results.

While inflammation was decreased in these treatment groups, we observed a greater effect for these drugs in prevention of bone and cartilage destruction than on joint swelling. FIGS. 1A-1E show that radiographic analysis of the ankle joints revealed that vehicle-treated arthritic rats had visible soft tissue swelling, bone loss, periosteal bone formation, narrowing of their joint spaces, and a decreased bone density by day 28 (FIG. 1A-F). Radiographic scores were significantly reduced with all adrenergic treatments compared with the vehicle controls (H=13.74, df=3: Phentolamine (P<0.05), Terbutaline (P<0.05), or SH1293 (P<0.01)) (FIG. 1F). Lower radiographic scores in phentolamine or terbutaline treatment groups reflected a reduction in the amount of soft tissue swelling, bone loss, and joint space narrowing. Terbutaline or phentolamine treatment resulted in an ~50% or 51% decrease in bone loss, respectively, compared to vehicle-treated AA rats. However, the most dramatic effects on bone and cartilage loss were observed in the combination phentolamine and terbutaline treatment, as they demonstrated an ~60% reduction in radiographic scores compared to vehicle-treated AA animals. Although the differences in radiographic scores compared between the adrenergic drug treatments were not significant, this trend for the combination of phentolamine and terbutaline to be more effective in preventing bone loss has been consistent in repeat experiments (FIG. 1F). These dramatic bone sparing effects following the adrenergic drug treatments are illustrated in the radiographs (FIG. 1A-E). An x-ray of a normal non-arthritic joint (FIG. 1A) is included for comparison.

EXAMPLE 2

Combined $\beta_2$-Adrenergic Agonist (Terbutaline) and ●-Adrenergic Antagonist (Phentolamine) Treatment Promotes an Anti-inflammatory Cytokine Profile in the Secondary Immune Organs and Peripheral Blood Mononuclear Cells 1. Method To determine if the adrenergic drug treatments were able to modify cytokine patterns in the secondary lymphoid organs and systemically in the blood, pro- and anti-inflammatory cytokine profiles were obtained ex vivo from cells harvested from the draining (inguinal and poplitial) lymph nodes, spleen and the PBMC from the animals described above.

All tissue culture media and supplements were obtained from Gibco BRL (Rockville, Md.) unless otherwise stated. OPTIA sandwich ELISA kits for IL-10 and TNFα were purchased from Pharmingen (San Diego, Calif.).

The spleen and lymph nodes were aseptically removed from the animal and placed into Hank's balanced salt solution (HBSS). The spleens were placed in a stomacher bag and homogenized for 30 seconds. Spleen cells were triturated with a 10 ml pipette then washed with an additional 10 ml of HBSS and passed through a nylon mesh (Marsh Industries) to remove the extraneous connective tissue. The collected cells were centrifuged and re-suspended in 5 ml of a $NH_4Cl$ hypotonic buffer for 3 min to lyse the red blood cells. The cells were washed 2× with 10 ml HBSS, centrifuged and re-suspended into complete RPMI 1640 media supplemented with 5% fetal calf serum and 1% antibiotic/antimycotic.

The draining (inguinal and poplitial) lymph nodes were placed into sterile etri dishes containing 5 ml HBSS. The lymph nodes were teased apart using forceps and triturated with a pipette. The homogenates then were passed through a nylon mesh, centrifuged and re-suspended in 5 ml HBSS. The cells then were centrifuged and re-suspended into complete RPMI 1640 media supplemented with 5% fetal calf serum and 1% antibiotic/antimycotic.

PBMCs: Blood was collected using cardiac puncture into a 7 ml lithium heparin vaccutainer tubes. The tubes were inverted 7 times and then spun down at 1000 rpm for 15 minutes at 10° C. The buffy coat was removed using a 2 ml pipette and placed into a sterile 15 ml tube containing 10 ml of a $NH_4Cl$ hypotonic buffer for 3 min to lyse the red blood cells. The peripheral blood mononuclear cells (PBMC) were centrifuged and re-suspended in 10 ml HBSS. The PBMC were washed three more times with 10 ml HBSS, centrifuged and re-suspended into complete RPMI 1640 media supplemented with 5% fetal calf serum and 1% antibiotic/antimycotic.

The prepared cells were counted using a hemocytometer, then brought to the concentration of 2×10^6 cells/ml. Two ml of the cell preparation were plated into 24 well plates (Falcon, Oxnard, Calif.), and in placed in an incubator 7% $CO_2$, 37° C., for 24 h. After 24 h the culture supernatants were harvested and placed in the freezer at −70° C. until ELISA assay.

Optia kits for the detection of IL-10 and TNFα were obtained from BD Pharmingen (Los Angeles, Calif.) and sandwich ELISAs were used to measure the amount cytokine released into the culture media. In brief: High binding microtiter 96-well plates were pre-coated with 100 μl of capture antibody in coating buffer (0.1 M carbonate buffer, pH 9.5) for IL-2, IL-4, IFNγ and TNFα and (0.2 M phosphate buffer, pH 6.5) for IL-10. The plates were sealed with plate film (Denville Scientific, South Plainfield, N.J.) and placed at 4° C. overnight. The plates were allowed to come to room temperature and washed with 0.1 M phosphate buffered saline-0.5% Tween 20 (PBS-Tw20).

The non-specific binding was blocked using PBS-Tw20 and 1% bovine serum albumin. Standard/sample was then added to each well, the plates were sealed and incubated overnight at 4° C. The plate was washed three times with PBS-Tw20 and biotinylated secondary detection antibody and streptavidin/avidin enzyme conjugate (diluted in PBS-1% bovine serum albumin) were added to the wells and the plates incubated for 1.5 h. The plates were then washed and developed with (TMB) reagent (Pharmingen, San Diego, Calif.) for 30 minutes.

After color development the plates were stopped with addition of IN sulfuric acid. Unknown sample cytokine levels were determined through comparison with a standard curve present on each plate using an ELISA reader (Ceres 900 HDI: Bio Tek Instruments Incorporated, Winooski, Vt.). The concentrations were averaged for each treatment group at each time point, expressed as mean±SEM in ng/ml, and subjected to a one-way ANOVA (p<0.05) with Newman-Keuls post-hoc testing.

Differences in cytokine production levels between treatment groups were determined by a one-way analysis of variance (ANOVA) for multiple groups. Means found to be significantly different were subjected to a Bonferroni Multiple Comparison Test (t values are reported with the level of significance) post-hoc analysis to determine the source of the variance.

2. Results

| Ratios of IL-10/TNFα Following Adrenergic Drug Treatments | | | | |
|---|---|---|---|---|
| Tissue/Rx | Vehicle | Phentolamine | Phen/Terb | Terbutaline |
| PBL | 0.2161 ± 0.0315 | 0.8067 ± 0.1762 | 1.2110 ± 0.0446* | 0.4382 ± 0.0471 |
| DLN | 0.9642 ± 0.1980 | 1.0960 ± 0.1961 | 0.8854 ± 0.2122 | 1.5060 ± 0.1642 |
| SPL | 0.4090 ± 0.0719 | 3.3350 ± 0.6716* | 5.0490 ± 1.0690@ | 2.1370 ± 0.8285 |

Statistical analysis: One-way ANOVA with Bonferroni Multiple Comparison Test. N = 6,
*P < 0.05;
@P < 0.001 compared with vehicle treated animals.

These data demonstrate that following phentolamine treatment alone and in combination with terbutaline treatment there is an increase in the ratio of anti- to pro-inflammatory cytokine production by macrophage cells in the secondary lymphoid organs and peripheral blood. These data demonstrate that adrenergic drug treatment reduces the amount of inflammatory mediators and provide a potential mechanism through which these drugs could be having their beneficial effects.

EXAMPLE 3

Combined $\beta_2$-Adrenergic Agonist (Terbutaline) and the Non-Specific $\alpha$-Adrenergic Antagonist(Phentolamine), the Specific $\alpha_1$-Adrenergic Receptor Antagonist (prazosin) or the Specific $\alpha_2$-Adrenergic Receptor Antagonist (Yohimbine) Suppression of Adjuvant-Induced Arthritis in Rats 1. Method Lewis rats with AA were used to determine if the anti-inflammatory and bone sparing properties of the combination treatment described above were being mediated by blocking the $\alpha_1$- and/or $\alpha_2$-AR subtypes. AA was induced in adult male Lewis rats as described above. Phentolamine (a non-specific $\alpha$-AR antagonist), prazosine (an $\alpha_1$-AR antagonist), yohimbine (an $\alpha_2$-AR antagonist) and terbutaline (a $\beta_2$-AR agonist) were obtained from Sigma Chemical Company (St. Louis, Mo.). All of the adrenergic drugs were dissolved in 0.01 mM ascorbic acid in 0.9% sterile, endotoxin-free saline. Adrenergic therapy with phentolamine and/or terbutaline, prazosine and/or terbutaline, yohimbine and/or terbutaline or vehicle was started on day 12 post-immunization, the time of disease onset, and continued until sacrifice. The dose of phentolamine (500 μg/day), prazosine (2.5 mg/day), yohimbine (750 μg/day) and/or terbutaline (600 μg/day) were administered by i.p. injections twice a day in a total volume of 500 μl per injection.

The inflammatory response in the arthritic rats was assessed and analyzed as described above. The animals were sacrificed when significant differences between the dorsoplantar footpads of the groups became apparent in the late effector phase, 28 days post-adjuvant injection. Radiographic analysis was also completed and analyzed as described previously. This experiment was replicated twice. Protocols for the use and care of the animals in the study were approved prior to beginning the experiments by the Sun Health Research Institute Animal Use and Care Committee and complied with NIH guidelines for the humane use and care of research animals.

2. Results a. Footpad Measurements from Arthritic Rats Started on Adrenergic Drugs on Day 12

Continuous treatment of combination adrenergic drug therapies from disease onset affected dorsoplantar footpad widths in arthritic rats. All CFA-challenged rats developed AA between days 10-12. As shown in FIG. 3, soft tissue swelling was significantly decreased in yohimbine/terbutaline-, phentolamine/terbutaline- and prazosine/terbutaline-treated animals compared with the vehicle-treated AA rats by day 28 post-adjuvant injection (Yohimbine/terbutaline: $F_{11,84}$=17.21, Day 28: $t_{Yoh/Terb}$=3.353, P<0.05) (Phentolamine/Terbutaline: $F_{11,84}$=21.05, Day 24: $t_{Phen/Terb}$=3.330, P<0.05; Day 26: $t_{Phen/Terb}$=2.975, P<0.05; Day 28: $t_{Phen/Terb}$=3.312, P<0.05) (Prazosin/Terbutaline: $F_{11,84}$=88.42, Day 20: $t_{Praz/Terb}$=3.403, P<0.05; Day 22: $t_{Praz/Terb}$=4.312, P<0.001; Day 24: $t_{Praz/Terb}$=5.747, P<0.001; Day 26: $t_{Praz/Terb}$=5.297, P<0.001; Day 28: $t_{Praz/Terb}$=6.353, P<0.001). These findings were replicated twice with similar results.

b. Radiographic Scores from Arthritic Rats Started on Adrenergic Drugs On Day 12

As shown in FIG. 4A-E, radiographic analysis of the ankle joints revealed that vehicle-treated arthritic rats had visible soft tissue swelling, bone loss, periosteal bone formation, narrowing of their joint spaces, and a decreased bone density by day 28. Radiographic scores were significantly reduced with these adrenergic treatments compared with the vehicle controls (H=17.78, df=3: combined phentolamine and terbutaline (P<0.05), combined prazosin and terbutaline (P<0.001). Lower radiographic scores in phentolamine/terbutaline and prazosine/terbutaline treatment groups reflected a reduction in the amount of soft tissue swelling, bone loss, periosteal bone formation and joint space narrowing (FIG. 4F). These dramatic bone sparing effects following the adrenergic drug treatments are illustrated in the radiographs in FIG. 4A-E.

EXAMPLE 4

There is an Noradrenergic Nerve Injury/Sprouting Response which Occurs in the Spleen of AA Rats with Disease Development 1. Methods Arthritis was induced in Lewis Rats using a single base of the tail interdermal injection of complete Fruend's adjuvant as described above.

a. Glyoxylic Acid Method of Histofluorescence for Catecholamines

On day 28 post adjuvant injection the rats were given an anesthetic overdose of 8% chlorohydrate prior to removal of their spleen tissue. Spleens from arthritic and non-arthritic rats were rapidly isolated and the blood vessels entering the spleen visualized. The spleen and blood vessels were dissected. NA nerves enter the spleen in association with the blood vasculature (hilar regions). To obtain hilar regions, parallel cross-sectional cuts were made on either side of these blood vessels. Distal regions were taken between these blood vessels. Hilar and distal cross-sectional blocks were quickly frozen on dry ice and stored at −70° C. until further processing.

Fresh frozen sections from hilar and distal pieces of spleen were cut at a thickness of 16 μm on a cryostat at −20° C. Sections were melted onto gelatin coated slides and prepared for histofluorescence for localization of the catecholamines using a modification of the glyoxylic acid condensation method (SPG). Three sections were mounted on each slide and immediately dipped into glyoxylic acid. Dipped sections were air dried under a stream of cold air using a blow dryer for 15 minutes. Spleen sections were covered with several drops of mineral oil and the slide placed on a copper plate in the oven at 95° C. for 2.5 minutes. Sections were examined and photographed on a Zeiss fluorescence microscope equipped with epi-illumination accessories.

b. Morphometric Analysis

For quantification NA fiber density in the spleens from AA and non-AA rats, one white pulp and one red pulp region from three different spleen sections form the hilar and distal region from 4 animals per groups was randomly selected. In the hilar sections, the white pulp and red pulp region was selected from an area 0.25 mm on either side of the apex of the spleen section. The distal sections, the white pulp and red pulp areas chosen for assessment were taken within 1 mm from either base point of the triangular spleen sections. Red pulp areas used for assessment entirely filled the photographic frame. White pulps in the hilar and distal regions had fairly uniform diameters of their central arterioles.

Central arteriole diameters ranged from 140 to 250 μm in hilar sections and 70 to 130 μm in distal sections in white pulp areas used to determine the volume density of NA fibers. The mean diameter for white pulp central arterioles in hilar sections for non-arthritic and arthritic rats was 182.02±6.43 μm and 178.06±3.10 μM, respectively (means expressed as MEAN standard error of the mean). In distal sections, the mean diameter of the central arterioles for the non-arthritic and arthritic rats was 95.59±5.18 μm and 94.22±0.85 μm, respectively. An attempt was made to select white pulps, to be used in assessing NA terminal volume densities between treatment groups, so that the cut across the central artheriole was in cross-section.

The volume density represents the volume of NA nerve terminals contained within the unit volume of one photographic frame expressed as a percentage, using the general formula for volume density: Vva,c=Pa/Pc×100, where Pc is the total volume of the tissue within the photographic frame (c) and Pa is the volume of NA nerve terminals (a) within the tissue area of the photographic frame. All fluorescent profiles in a single white pulp or red pulp area from hilar and distal sections were photographed at the same magnification (50×; selected such that a single white pulp filled the frame) as a single 35 mm slide.

Slides were projected onto a grid, 10×10 squares per inch using an Aus Jena viewing scope set to magnify the section 13×. The size of the grid was based on the assumption that one NA varicosity would fill the area of a single square of the grid. The lines of the intersections on the grid in which the NA fluorescent nerve profiles projected were counted. Points of intersection from all of the slides from each section of spleen were totaled. The percent volume density of the NA profiles per spleen was calculated based upon the actual magnification of the profiles when projected onto the screen, the size of the grid, and the volume density of each white or red pulp area taken from each section. The differences in volume density of NA fibers among the two groups were analyzed by using a Student's t-Test (P<0.05).

2. Results

The volume density of the NA nerves in the white pulp regions from the hilar spleen sections was increased in the arthritic rats compared to the non-arthritic rats (FIG. 5A). In contrast, in the distal regions of the spleen, there was a reduction in the volume of NA nerves from the arthritic rats compared with the non-arthritic animals (FIG. 5A). Additionally, in the red pulp regions from spleen sections from the hilar and distal regions there was a sprouting of nerve fibers into the red pulp regions of the arthritic animals compared to the non-arthritic animals (FIG. 5B).

These data support an injury response is taking place in the white pulp region followed by a subsequent sprouting response of these NA fibers into the red pulp regions. This nerve remodeling could have dramatic functional consequences, as the nerves are now potentially signaling immune cell populations which are at different activation states; thereby, could express different ratios of adrenergic receptor subtypes.

While the invention has been described with reference to a particular embodiment, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as best mode contemplated for carrying out this invention, but that the invention will include all embodiments falling within the scope of the appended claims.

We claim:

1. A method for treating rheumatoid arthritis in an animal comprising:
   administering to an animal a therapeutically effective dose of a composition comprising an α-adrenergic antagonist; and a β-adrenergic agonist; wherein inflammation in the animal is suppressed and joint destruction in the animal is suppressed.

2. The method in claim 1, wherein the inflammation is decreased.

3. The method in claim 1, wherein the α-adrenergic antagonist is an $\alpha_1$-adrenergic antagonist.

4. The method in claim 1, wherein the α-adrenergic antagonist is an $\alpha_2$-adrenergic antagonist.

5. The method in claim 1, wherein the α-adrenergic antagonist is selected from the group consisting of yohimbine, regitine, prazosin, doxazosin, tamsulosin, terazosin, octopamine, phenoxybenzamine, phentolamine, hydrochlorothiazide, 5-methyl urapidil, chloroethylclonidine, bunazosin, alfuzosin, urapidil, nicergoline, cyclazosin, fiduxosin, imiloxan, 2 idopropoxyidazoxan, 2-methoxyidazoxan, idazoxan, piperoxan, beditin, atipamezole, rawolscine, and ethoxyidazoxan.

6. The method in claim 1, wherein the β-adrenergic agonist is a $\beta_2$-adrenergic agonist.

7. The method in claim 1, wherein the β-adrenergic agonist is selected from the group consisting of terbutaline, metaproterenol, albuterol, isoetharine, pirbuterol, bitolterol, ritodrine, and salbutamol.

8. The method in claim 1, wherein the therapeutically effective dose of the composition comprises 1.0 to 10.0 mg of α-adrenergic antagonist and 1.0 to 10.0 mg of β-adrenergic agonist.

9. The method in claim 1, wherein the therapeutically effective dose of the composition comprises 2.0 to 5.0 mg of α-adrenergic antagonist and 2.0 to 5.0 mg of β-adrenergic agonist.

10. The method in claim 1, wherein the therapeutically effective dose of the composition comprises 1.25 to 2.5 mg of α-adrenergic antagonist and 1.25 to 2.5 mg of β-adrenergic agonist.

11. The method in claim 1, wherein the animal is a mammal.

12. The method in claim 11, wherein the mammal is a human.

13. The method of claim 1, wherein the composition is administered in a form selected from the group consisting of pill, tablet, capsule, caplet, solution, suspension, syrup, suppository, and aerosol.

14. The method of claim 1, wherein the composition is administered in a sustained-release form.

15. The method of claim 1, wherein the route of administration is selected from the group consisting of sublingually, orally, intravenously, intramuscularly, rectally, parenterally, subcutaneously, and subdermally.

16. The method of claim 1, wherein the β-adrenergic agonist is administered in salt form.

17. The method of claim 16, wherein the β-adrenergic agonist salt form is selected from the group consisting of metaproterenol sulfate, terbutaline sulfate, albuterol sulfate, ioetharine hydrochloride, isoetharine mesylate, pributerol acetate, bitolterol mesylate, ritodrine hydrochloride, levalbuterol hydrochloride, and salmeterol.

18. The method of claim 1, wherein the α-adrenergic antagonist is administered in salt form.

19. The method of claim 18, wherein the α-adrenergic antagonist salt form is selected from the group consisting of phentolamine mesylate, regitine mesylate, prasozin, terazosin, doxazosin mesylate, and tamsulosin hydrochloride.

20. The method of claim 1, wherein the therapeutically effective dose is administered two times per day.

21. The method of claim 1, wherein the therapeutically effective dose is administered three times per day.

22. The method of claim 1, wherein the therapeutically effective dose is administered more than three times per day.

23. A method for treating rheumatoid arthritis comprising:
administering to an animal an α-adrenergic antagonist; and
administering to an animal a β-adrenergic agonist; wherein joint destruction in the animal is suppressed.

24. The method of claim 23, wherein the β-adrenergic agonist is administered followed by the α-adrenergic antagonist 25. The method of claim 23, wherein the α-adrenergic antagonist is administered followed by the β-adrenergic agonist.

26. The method of claim 23, wherein the α-adrenergic antagonist and β-adrenergic agonist are administered in the same 24-hour time period.

27. The method of claim 23, wherein the α-adrenergic antagonist and β-adrenergic agonist are administered in the same one-hour time period.

28. A method for treating rheumatoid arthritis in an animal, comprising administering to the animal a composition comprising phentolamine and terbutaline.

29. The method of claim 28, wherein the compound comprises 1.0 to 10.0 mg of phentolamine.

30. The method of claim 28, wherein the compound comprises 1.0 to 10.0 mg of terbutaline.

31. The method of claim 28, wherein the compound is administered more than one time per day.

* * * * *